United States Patent [19]

Davidson et al.

[11] Patent Number: 4,958,295

[45] Date of Patent: Sep. 18, 1990

[54] ANALYZING APPARATUS AND METHOD FOR ANALYSIS OF LIQUID SAMPLES

[75] Inventors: David L. Davidson, Newark, Del.; George B. Parrent, Jr., Chelmsford; Roland W. Gubisch, Lexington, both of Mass.; Harold Hauer, Wilmington, Del.

[73] Assignee: Hercules Incorporated, Wilmington, Del.

[21] Appl. No.: 409,277

[22] Filed: Sep. 19, 1989

Related U.S. Application Data

[63] Continuation of Ser. No. 249,261, Sep. 22, 1988, abandoned, which is a continuation of Ser. No. 865,889, May 21, 1986, abandoned.

[51] Int. Cl.$^5$ .............................................. G01N 30/04
[52] U.S. Cl. ..................................... 364/497; 422/82; 422/67; 436/53
[58] Field of Search ............... 364/497, 498, 500, 502, 364/510; 422/56–58, 62, 67, 68, 70, 81, 82; 73/61.1 C, 61.1 R; 436/52, 53

[56] References Cited

U.S. PATENT DOCUMENTS

| | | | |
|---|---|---|---|
| 3,047,367 | 7/1962 | Kessler | 23/230 |
| 3,098,717 | 7/1963 | Ferrari, Jr. | 23/230 |
| 3,118,735 | 1/1964 | Favre et al. | 23/230 |
| 3,174,344 | 3/1965 | Haruka | 73/422 |
| 3,195,355 | 7/1965 | Boyer | 73/422 |
| 3,241,432 | 3/1966 | Skeggs et al. | 88/14 |
| 3,282,651 | 11/1966 | Ferrari et al. | 23/253 |
| 3,306,229 | 2/1967 | Smythe | 103/149 |
| 3,365,951 | 1/1968 | Jentzsch et al. | 73/422 |
| 3,461,030 | 8/1969 | Keyes | 162/198 |
| 3,540,982 | 11/1970 | Sepall | 162/253 |
| 3,607,073 | 9/1971 | Stamm | 364/502 |
| 3,842,679 | 10/1974 | Iwao et al. | 73/423 A |
| 3,926,561 | 12/1975 | Lucero | 23/232 R |
| 3,985,508 | 10/1976 | Williams | 23/253 R |

(List continued on next page.)

FOREIGN PATENT DOCUMENTS 0180063 5/1986 European Pat. Off. .
0229599 7/1987 European Pat. Off. .
61-82169 4/1986 Japan .

OTHER PUBLICATIONS

Proceedings of the Royal Society, Series A, vol. 219, 1953, pp. 186–203.

*Primary Examiner*—Parshotam S. Lall
*Assistant Examiner*—V. N. Trans
*Attorney, Agent, or Firm*—Connolly & Hutz

[57] ABSTRACT

A liquid stream (13) and a detector (12) and a computer (11) which operate to observe properties in the composition of the fluid stream and compare detected data from observed samples with standards and in accordance with parameters established by calibration calculate the characteristics of the observed samples.

An integral but segmented liquid stream (13) flows through the analysis system (10) to provide liquid segments of observed sample and reagent. A detector (12) scans data from the samples at the interface between these segments and information relating to the composition at the interface is analyzed by a mathematical model that permits comparison of the detected data from successively observed samples with standards and thus determines the characteristics of the samples. The segmented integral liquid stream (13) is fashioned by step pulsing of discrete segments of reagents and samples and transporting the discrete segments to a detector (12). The analysis system (10) is driven by a vacuum assembly (16) and valves to form the segments in the absence of air so that the respective sample and reagent segments interface with each other.

A plurality of source tanks (20) provide the liquid samples and reagents for the segmented, integral liquid stream (13) and the vacuum assembly (16) creates a force which forms and drives the samples and reagents through conduit means (21), (23), (27), (14) and (38) to the detector (12).

8 Claims, 23 Drawing Sheets

U.S. PATENT DOCUMENTS

| | | | |
|---|---|---|---|
| 4,009,999 | 3/1977 | Negersmith | 422/82 |
| 4,013,413 | 3/1977 | Stewart | 23/230 R |
| 4,055,752 | 10/1977 | Kappe et al. | 364/551 |
| 4,108,602 | 8/1978 | Hanson | 23/230 R |
| 4,169,125 | 9/1979 | Rodriguez et al. | 364/497 |
| 4,177,677 | 12/1979 | Ruzicka et al. | 73/422 G C |
| 4,224,033 | 9/1980 | Hansen et al. | 23/230 R |
| 4,227,973 | 10/1980 | Ruzicka et al. | 204/1 T |
| 4,259,079 | 3/1981 | Blum | 422/81 |
| 4,283,201 | 8/1981 | DeFord et al. | 422/82 |
| 4,314,824 | 2/1982 | Hansen et al. | 23/230 R |
| 4,315,754 | 2/1982 | Ruzicka et al. | 422/81 |
| 4,352,780 | 10/1982 | Schick | 422/81 |
| 4,399,225 | 8/1983 | Hansen et al. | 436/34 |
| 4,442,217 | 4/1984 | Deans | 436/161 |
| 4,472,352 | 9/1984 | Passell et al. | 422/62 |
| 4,502,938 | 3/1985 | Covington et al. | 204/412 |
| 4,504,443 | 3/1985 | Hansen et al. | 422/81 |
| 4,511,659 | 4/1985 | Matson | 73/61.1 C |
| 4,512,953 | 4/1985 | Marsoner et al. | 422/67 |
| 4,517,302 | 5/1985 | Saros | 436/180 |
| 4,520,108 | 5/1985 | Yoshida et al. | 422/81 |
| 4,557,601 | 12/1985 | Kuroishi et al. | 356/320 |
| 4,577,492 | 3/1986 | Holba et al. | 73/61.1 C |

ANALYZING APPARATUS AND METHOD FOR ANALYSIS OF LIQUID SAMPLES

The application is a continuation of application Ser. No. 249,261, filed Sept. 22, 1988, now abandoned, which is a continuation of application Ser. No. 865,889, now abandoned, filed on May 21, 1986.

BACKGROUND OF THE INVENTION

The present invention relates to an a analysis apparatus or system for rapid analysis of liquid samples, or more particularly to an apparatus and method for performing analysis of multiple samples in which the multiple samples are selectively introduced into an analysis path and rapidly and precisely individually analyzed. Still more particularly, this invention relates to a programmable analysis of individual samples in an integral stream of liquid.

DESCRIPTION OF THE PRIOR ART

Analysis by flow injection analysis, FIA, provides that a liquid sample of small volume is injected into a carrier stream so that the injected sample forms a zone. This zone of the sample disperses in the carrier and is subject to examination in a detector. Typically in a system of this type the sample reacts with the carrier forming a product which is sensed in a detector and the sensed data recorded. The recorded information takes the form of a peak curve registered on a suitable recording device. Typically the shape of the recorded curve is an unsymmetrical peak, with height and width defined by a leading edge, a peak and a following edge. The leading and following edges of the interface between the sample zone and the carrier define the shape of the curve for a given sample. In this previous analytical technique only the height or width of these curves are used to judge the concentrations of successively detected and observed samples. Thus, very little of the available information is used.

The success of the FIA technique depends upon the controlled dispersion of the sample and/or reagent in the carrier stream to influence the rates of chemical reactions and to adjust the concentrations of reacting species to optimize detector response. The dispersion is a function of the ratio of the size of the injected aliquot to the volume of the reaction zone, the geometry of the flow path, the velocity of the carrier stream, and the molecular diffusivity of the species in question. As the geometry of the flow path and the velocity of the carrier stream are dictated by commercially available pump and tubing sizes, practitioners of flow injection analysis use the sample/reagent aliquot size to adjust the observed dispersion to the desired detector response (curve shape).

An automated sampling system in which samples are drawn into the system using a vacuum pump through a sample selector valve was disclosed by Hanson et al U.S. Pat. No. 4,108,602. The samples are drawn from the selector valve through a flow cell of a chemical analyzer. Flow is then allowed to continue past the flow cell to an overflow section where liquid flow is blocked by a microporous filter to protect the source of partial vacuum. After analysis, the sample is returned through the same selector valve by switching from a vacuum system to a pumping system. First and second flow paths within the analyzer system are provided which can be used for measuring sample and additive quantities. A means for mixing measured quantities of sample and additive is provided.

A flow injection analysis system where the flow is stopped intermittently was disclosed by Ruzicka et al in U.S. Pat. No. 4,315,754. The process intermittently stops flow so that the reactions between the reagent and the sample may continue while the dispersion of the sample within the carrier stream is stopped by the cessation of movement of the carrier stream. This stoppage can take place either before or within the analyzer. The stoppage occurs in the analyzer when one wants to observe the reaction as it proceeds. The process requires a carrier stream and a discrete, well-defined liquid sample portion. The system calls for separate intermittently operated pumps to transport the carrier and injected sample to the analysis.

Saros discloses in U.S. Pat. No. 4,517,302 a sequence and coordination of system operations as well as calculating and monitoring the quality of results and providing data output in a variety of formats. In a continuous flow system, air or gas separates selected ones of the liquid segments.

SUMMARY OF THE INVENTION

It is an object of this invention to provide fluid injection analysis methods and devices which achieve excellent statistical accuracy and an economy in reagents. More particularly, it is an object of this invention to provide an analysis of a liquid sample using an increased number of observations in comparing successively tested samples against a standard and also increasing the rapidity of analysis. A still further object is to employ a mathematical model that permits the comparison of detected data from successively observed samples with standards.

It is a further object to provide means for creating an integral but segmented liquid stream flown through the analysis system.

Still another object is the use of the liquid integrity of a fashioned stream to provide liquid segments of the observed sample and a reagent.

It is also an object of this invention to provide an analytical means of determining composition of a sample from a dispersion of the sample at a single interface between the sample and a reagent.

The detectors sense and take measurements and from the parameters obtained in the calibration step calculate the characteristics of the tested sample. The combination of the sample with the reagent produces detectable change in the composition of the fluid stream at the interface of the two liquid segments. Readings by a suitable detector are taken in this zone of change. These detections may be electrical conductivity, pH or photometric sensors, for example.

Another object is increased capability of flow injection analysis.

An additional object is the use of and improved methods of operating an intermittent flow, segmented integral liquid stream, sample analysis apparatus, including a new means in flow sample analysis for reducing the number of valves and their operations.

In one combination in the present system this zone of change takes place at the interface between the slug of the reagent and the slug of the sample in a discrete, segmented liquid flow in which there is no constraint on the volume of the segments. By step pulsing, discrete segments of reagents and samples are fashioned and transported to a detector which scans data from the samples at the interfaces between the segments. The minimum size of a step pulse segment is such that nearly the original concentration of the fashioned segment appears at the detector. A typical detector response is illustrated in FIG. 3. The flow is controlled by a single valve positioned in the flow downstream from the detector. The force for moving the liquid flow is provided by a vacuum which draws the fluid through the system and the control valve.

The present development uses a static injection analysis process in which liquid samples to be analyzed and appropriate reagents are supplied through sample valves and reagent valves, respectively, to a sample manifold. The entire analysis system is driven by a vacuum pump connected to the end of the system through a vacuum valve. When the vacuum valve is closed no fluid flow takes place in the system. The sample valves and reagent valves are permitted to be operated from closed to open and vice versa only when the vacuum valve is closed. The vacuum valve is then opened to draw the sample or reagent through the manifold into the system. The volume of sample or reagent is determined by the period of time for which the vacuum valve is opened. All valves are operated under computer control in a pre-programmed sequence.

In addition to samples and reagents, the system can be provided with other inputs each connected through a valve to the manifold to provide fluids such as standard solutions, wash solutions, reactants and the like.

In a specific illustrated embodiment, the vacuum valve is opened. Sample is thus drawn by the vacuum pump into the system. When a sufficient amount of sample is drawn into the system the vacuum valve and sample valve are closed, in that order. A reactant valve is then opened in order to supply reactant to the manifold. The vacuum valve is then opened and the reactant is drawn into the system to mix with the sample. This sequence may be repeated for more samples and reactants as required.

The reacted sample forms an interface with a reagent admitted subsequent to all reaction. The interfaces thus created are then pulled by the vacuum pump through the system under laminar flow conditions past a detector cell which generates a signal proportional to the concentration of the unknown material. This measurement is taken continuously before, at, and after the interface passes the detector. The signal generated by the detector cell is then analyzed by a computer to determine the concentration of the unknown in the sample. The analysis is carried out using the fluid mechanical model for plug flow with axial dispersion.

An important aspect of the system is that the liquids are controlled in a manner so as to permit analysis using this fluid mechanical model. This is achieved by several devices used in the system. First, the reactant and sample are degassed immediately before use by passing the sample or reactants through a non-wetting tube of expanded polytetrafluoroethylene which is placed in a container under reduced pressure. The dissolved gases diffuse through the tube as the liquid is being drawn into the instruments. Second, the vacuum pump provides laminar flow free from perturbations. Lastly, zero dead-volume valving is used in the system to avoid the creation of dead volume which could trap reactant or sample, or introduce gases into the system.

In the illustrated embodiment, the sample is diluted by passing the sample over a nonwetting membrane which contains small pores. Back pressure in the system is used to force the sample through the pores into a diluent directly beneath the membrane. By varying the amount of back pressure used, the composition of the diluted solution can be precisely adjusted.

It is a feature of this system that no valve is turned on or off when flow is occurring through the system; that is, the vacuum valve is always turned off when other valves are operated. These conditions are provided to prevent gaps within the flowing liquid. Each analysis is thus performed at the interface of two liquids formed by the valving sequence. Therefore, it is not necessary to have uniformly sized samples and there is no constraint on volume.

DETAILED DESCRIPTION OF THE PREFERRED EMBODIMENT

Figure 1:
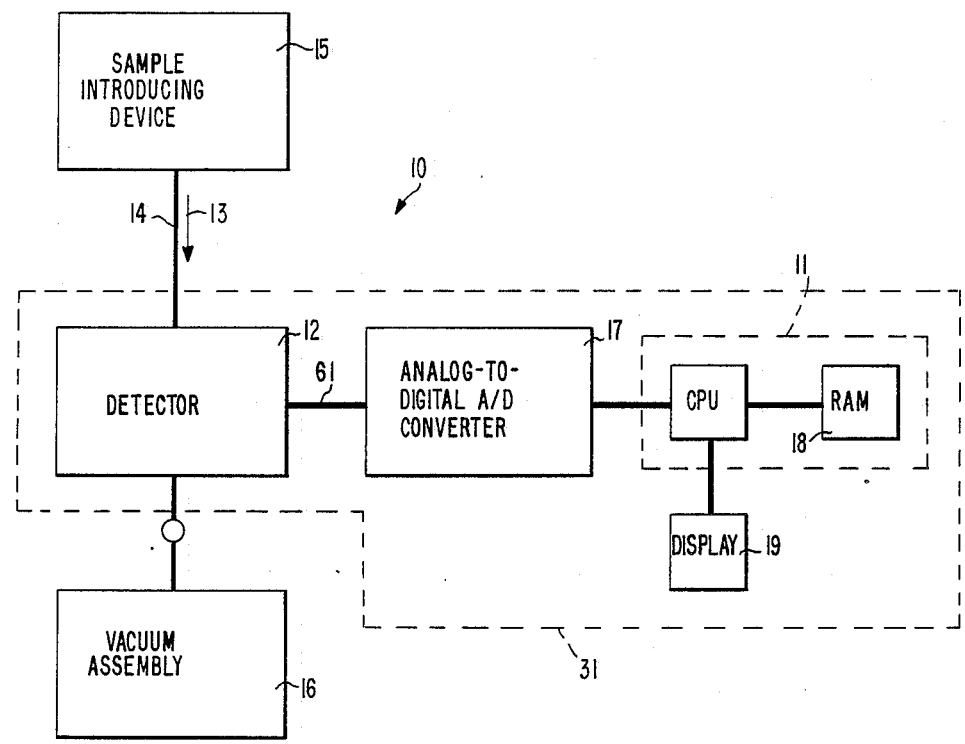
FIG. 1 is a block diagram for explaining the general functions of calibration and detection apparatus according to the present invention.

The diagram of FIG. 1 shows the apparatus. In the drawing, in analysis section 31, a computer 11 receives signals from a detector 12. In operation the segmented integral liquid stream 13 to be analyzed is passed to the detector through a tubing 14 from a sample introducing device 15. In the illustrated embodiment the liquid stream 13, represented by a directional arrow, is transported from the sample introducing device 15 to the detector 12 under the pull of a vacuum applied by a vacuum assembly 16 described in greater detail below. The detector 12 scans samples in the stream 13 for characteristics of the composition, such as concentration. The data observed in the detector 12 is transmitted to the computer 11 as digital signals through an analog to digital converter 17.

The computer 11 takes the detector signals and provides analyses of samples of liquid from that data. The calculations for the analysis are done by linear and nonlinear mathematical regression.

The data from the detector from the introduction of the standard is analyzed by the computer 11 using a nonlinear regression algorithm to determine the algebraic model parameters which characterize the flow system. These parameters are than subsequently used with a linear regression algorithm to determine the characteristics of the fashioned sample.

Figure 2:
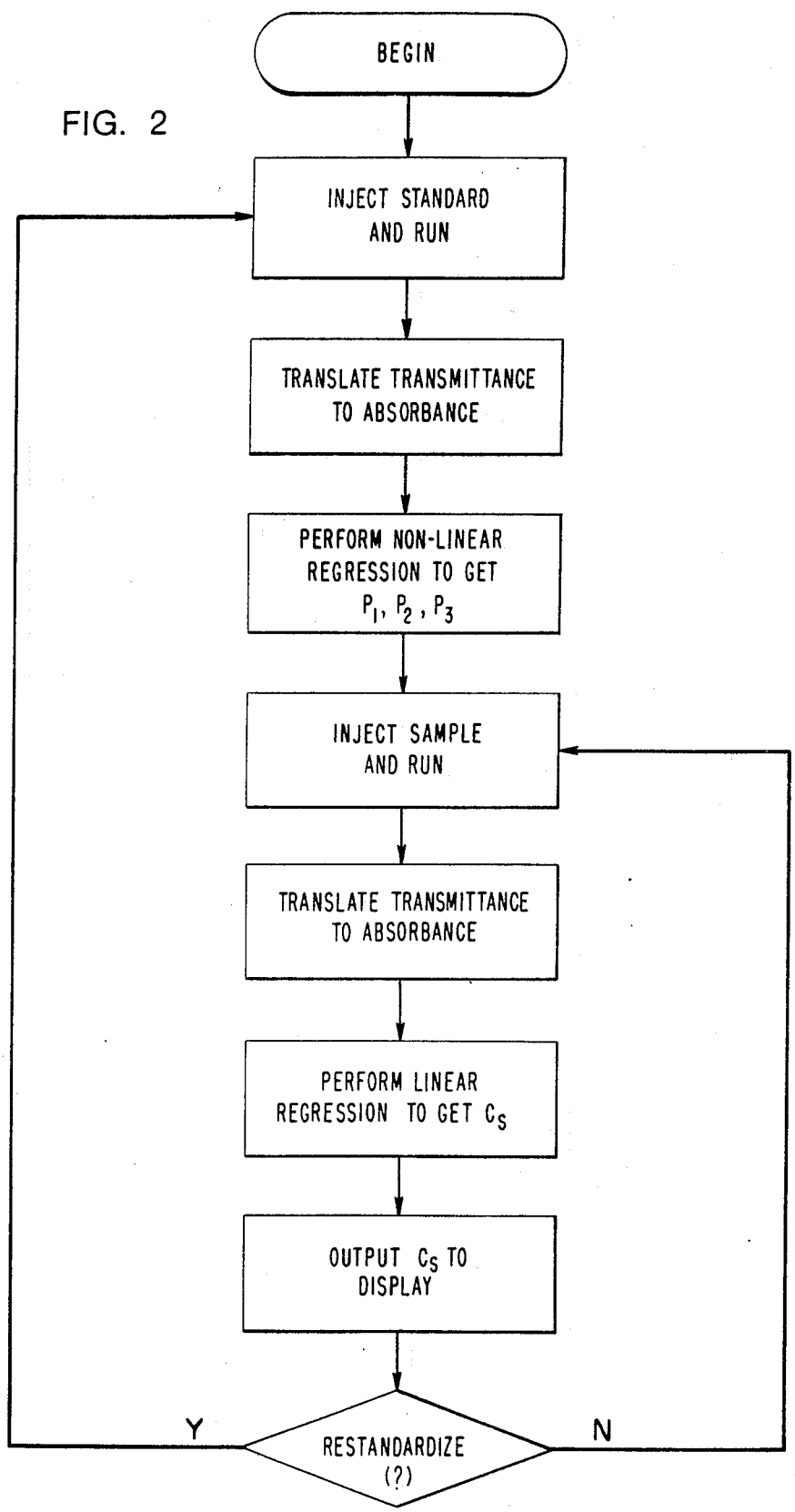
FIG. 2 is a flow chart of steps of the procedure to be followed when the apparatus according to this invention analyses samples impulse segments fashioned in the apparatus.

Reference is made to the sequence of events illustrated in FIG. 2. A step pulse segment of standard of known concentration is fashioned and the transmittance of radiation as the standard reagent interface passes by the detector is observed by the computer. This transmittance signal is stored in the computer's RAM 18, see FIG. 1 along with the elapsed time from the start of flow and subsequently converted to absorbance using the following equation.

$$Abs = \log_{10} T_o - \log_{10} T \qquad (1)$$

where $T_o$ is the transmittance of a perfectly clear and colorless solution and T is the observed transmittance.

A mathematical model which describes the interface is given by the following equation.

$$Abs = (\tfrac{1}{2})P_3 C^{std} \left[ 1 - erf\left( \frac{1 - t/P_2}{2\sqrt{P_1 t/P_2}} \right) \right] \qquad (2)$$

where the parameters $P_1$, $P_2$ and $P_3$ are determined by non-linear regression of the model over the absorbance-time data. Parameters $P_1$ and $P_2$ are known as the dispersion number and average resident time of the device and characterize the extent of dispersion in the tube. They are functions of the geometry of the system and not of the concentration of the introduced species. Parameter $P_3$ is simply the proportional constant that relates absorbance to concentration of the observed species of interest. It is precisely the determination of these parameters which constitutes instrument calibration.

The above equation 2 is shown for determining absorbance as the detected property, represented by the symbol Abs. In this equation when related to determining other properties the detected property may be represented by the symbol Y(t).

Similarly in equation 2, $c$Std is a symbol representing a standard specimen. In this equation when related to observing a sample specimen, the sample specimen may be represented by the symbol $C_o$.

Next a step pulse of sample of unknown concentration is fashioned and the transmittance of radiation as the sample/reagent interface passes by the detector is observed by the computer. This transmittance signal is stored in the computer's RAM 18 along with the elapsed time from the start of flow, and subsequently converted to absorbance using Equation 1. The same mathematical model that is used to perform the nonlinear regression is now used to calculate the sample concentration by performing a linear regression over the absorbance-time data for the sample. This results in an explicit expression for sample concentration:

$$C_s = \frac{\sum_{i=1}^{n} Abs_i X_i}{\sum_{i=1}^{n} X_i^2} \qquad (3)$$

$$X_i = \tfrac{1}{2} P_3 \left[ 1 - erf\left( \frac{1 - t_i/P_2}{2\sqrt{P_1 t_4/P_2}} \right) \right] \qquad (4)$$

Figure 3:
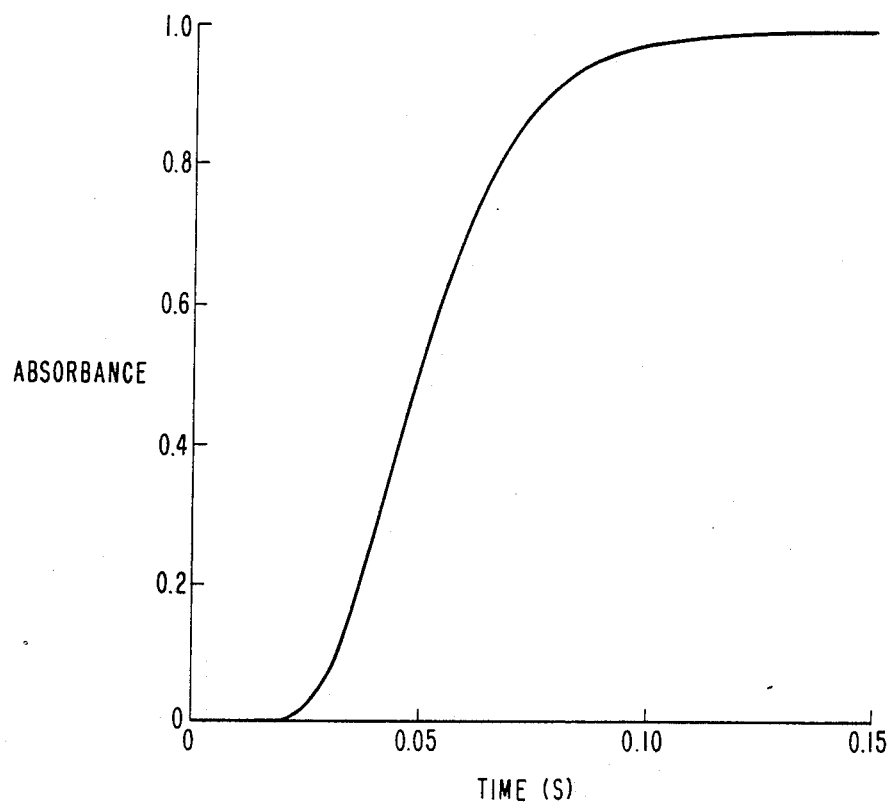
FIG. 3 is a graph illustrating a response curve in apparatus according to one embodiment of this invention.

The mathematical model of equation 2 describes a sigmoidal curve as illustrated by FIG. 3. This is a plot of the detector signal generated upon fashioning of a step pulse of standard or analyte adjustent to the reagent segment.

This plot illustrates the description of the standard/reagent interface and can be provided from the CPU on computer 11 on a display 19.

Figure 4:
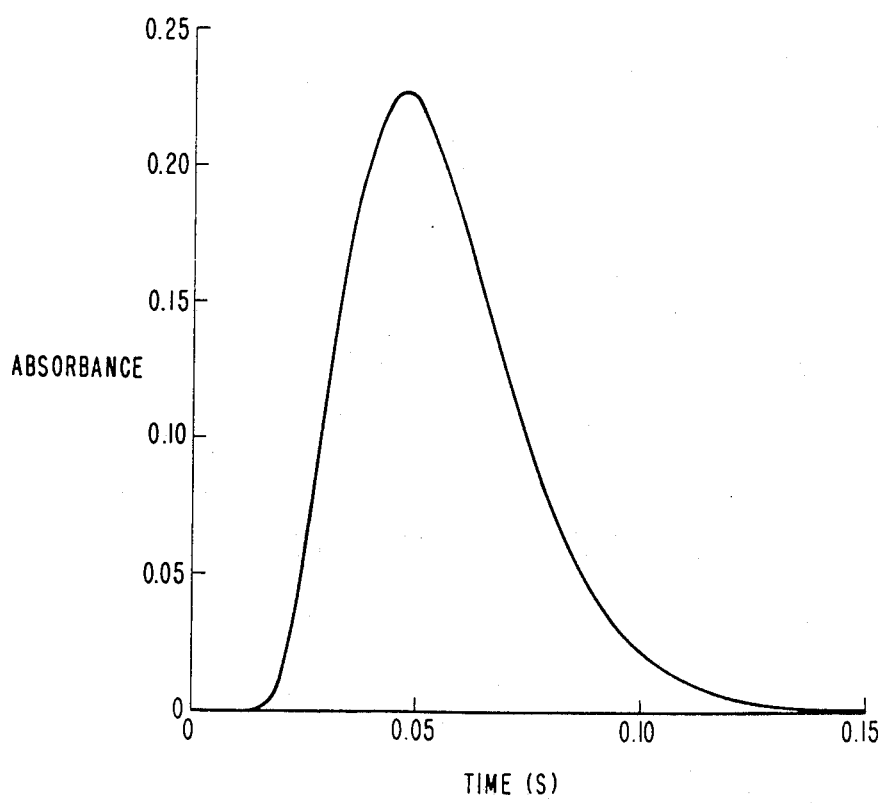
FIG. 4 is a graph illustrating a response curve in apparatus according to another embodiment of this invention.

The mathematical analysis procedure described above for the step pulse fashioning can be applied with equal facility to conventional FIA inpulse injection experiments, wherein the dispersion of the injection results in a peak curve typified by the curve in FIG. 4. In doing so, both the sequence of mathematical operations and regression algorithms are the same, while equation 2 is replaced by an expression representative of the smaller injection volume.

$$Abs = \tfrac{1}{2} CP_3 \left\{ erf\left[ \frac{\frac{\delta}{2P_2}(1 - t/P_2)}{2\sqrt{P_1 t/P_2}} \right] + erf\left[ \frac{\frac{\delta}{2P_2} + (1 - t/P_2)}{2\sqrt{P_1 t/P_2}} \right] \right\} \qquad (5)$$

where C represents the injected species concentration and $\delta$ the duration of the injection (expressed in units of time).

For disclosures providing procedures useful for methods for adjusting model parameters of the type described herein reference may be made to "Dispersion of Soluble Matter in Solvent Flowing Slowly Through a Tube", G.I. Taylor, Proceedings of Royal Society of London, Series A, Vol. 219, p. 186 (1953); a description of non-linear regression algorithms in "Optimum Seeking Methods", D.J. Wilde, Prentice Hall, N.Y., N.Y. (1964) pp. 145–150; and a description of statistical linear data regression in "Probability and Statistics for Engineers and Scientists", MacMillan, N.Y., N.Y., (1978), chap. 8.

It will be understood that it is a feature of the present invention that the mathematical regression calculations of the computer 11 are used to treat all of the rapidly collected points at the interfacial zone of the dispersion regardless of whether there is used the pulse segment portion or a well-defined impulse sample portion. These points are represented by the curves of FIGS. 3, 4, 8 to 23 and are used in analysis which is the object of this invention.

In an aspect of this invention the stream 13 in FIG. 1 is an entirely liquid stream, the flow of which is stopped intermittently and consists of segments fashioned in an integral liquid stream. The segments are referred to here as pulse segments as a representation of transient quantities brought about by an intermittent application of a transporting force from a vacuum.

The entirely liquid stream consists of pulse segments of liquid fashioned as described below by non-continuous flow, but united together at interfaces to become integrated into the integral liquid stream. Thus, the pulse segments are separate fragments of the stream each cut off from adjoining segments by an interface so as to provide a finite part of the stream usually between two other parts of the stream and thus being with the other segments the constituent parts making up the stream. It is a feature of this aspect of the invention that the useful and effective size of an analyzed sample has a very wide range, so that the size of the sample is not critical except that the sample portion must be of at least such a size that nearly the original concentration of the pulsed segment appears at the detector upon analysis of the interface at the detector. Stated otherwise, in fashioning a sample pulse segment for analysis, the shape or form of the slug making up the pulse segment must be such that the detector can observe the analyzed interface from a point where no subverting dispersion in the sample has taken place to the interface itself. The stream 13 as illustrated and described herein is identified as a segmented integral liquid stream. All the segments making the whole are liquid and the whole stream consists entirely of these liquid segments so that in fashioning the individual pulse segments, they are integrated to unite and form the complete stream.

Figure 6:
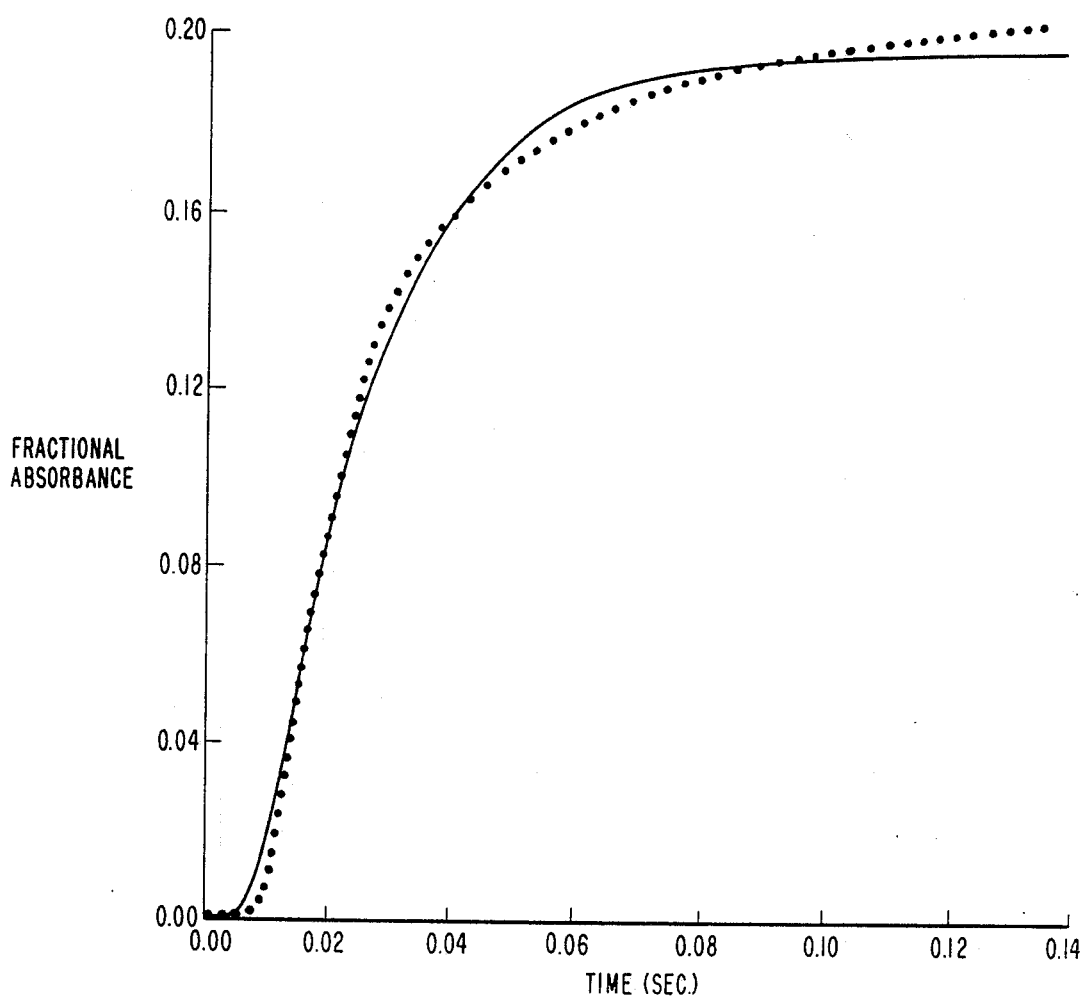
FIG. 6 is a graph charting readings taken according to this invention.

FIG. 6 shows the curve record for the readings obtained from the dispersion data observed from pulse segments fashioned in the system of FIG. 1. The recorded analyzed samples are detected at intervals of 270 μ sec. and the observed absorbance is recorded.

Referring to FIG. 5, there is shown a system for fashioning the pulse segments of a segmented integral liquid stream and transporting the stream to and through the detector to perform the single interface analysis in accordance with the present invention. Referring first to an embodiment of the sample introducing device 15, a multiple of samples and reagents are represented by storage in a number of tanks 20 from which the samples and reagents may be individually drawn through a plurality of tubings 21 to a connector board 22 where the samples flow into a plurality of tubings 23 of reduced diameter.

The samples and reagents are next processed through a degasser 24 to release the dissolved gas in the sample prior to further handling and the eventual analysis. The degasser 24 contains in a vacuum sealed housing 25, a porous tube 26 for each of the individual tubings 23 and its respective sample or reagent. As described in greater detail below, by adjusting the vacuum in housing 25 in relation to the porosity of the tubes 26 and the rate of stream flow, the liquid stream flow of the sample can be rendered substantially free of gas upon transport through delivery tubes 27 and zero dead volume valve 28. Typical tube sizes for tubes 23 and 27 and those throughout are 30 mil internal diameter.

Figure 5A:
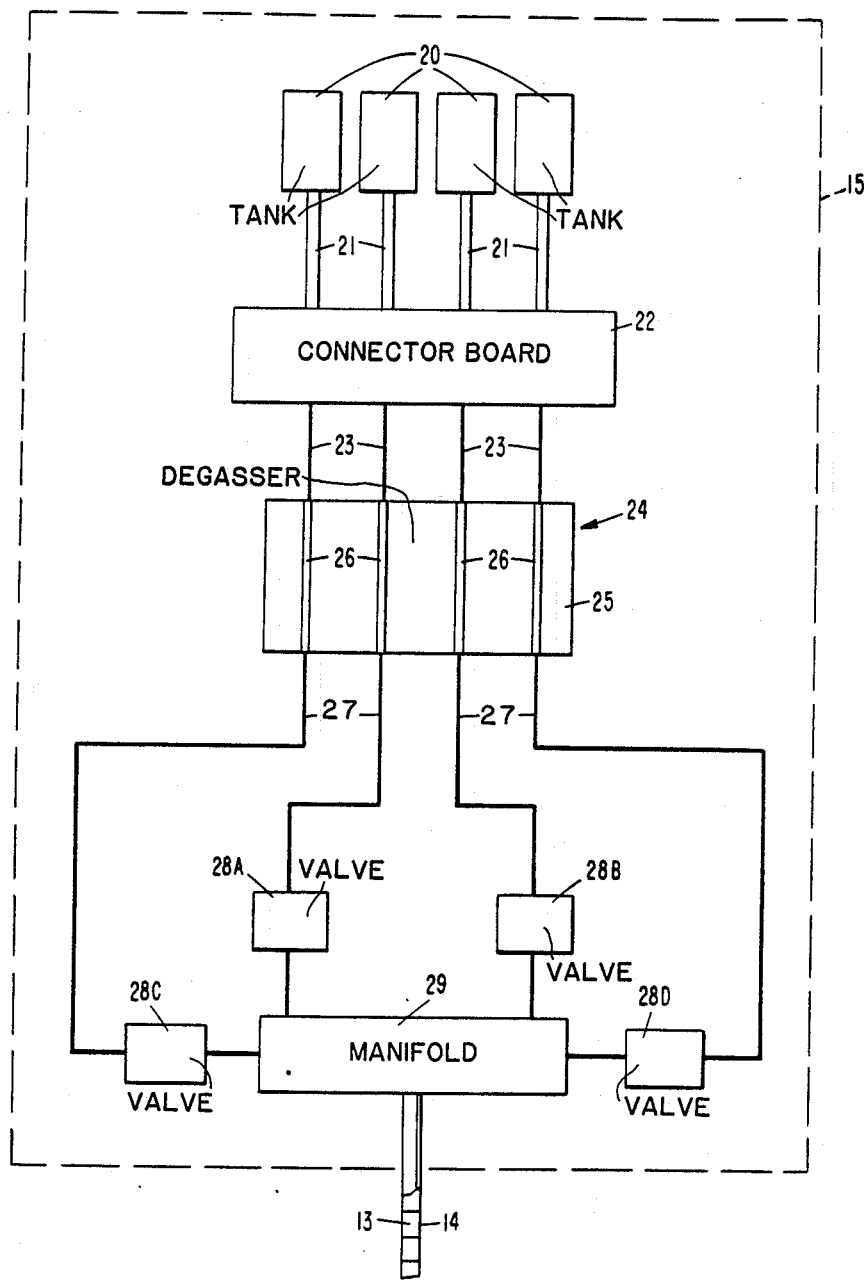
FIGS. 5A and 5B are views partly in section, illustrative of a system with an embodiment of this invention illustrative of the step pulse fashioning method.
Figure 5B:
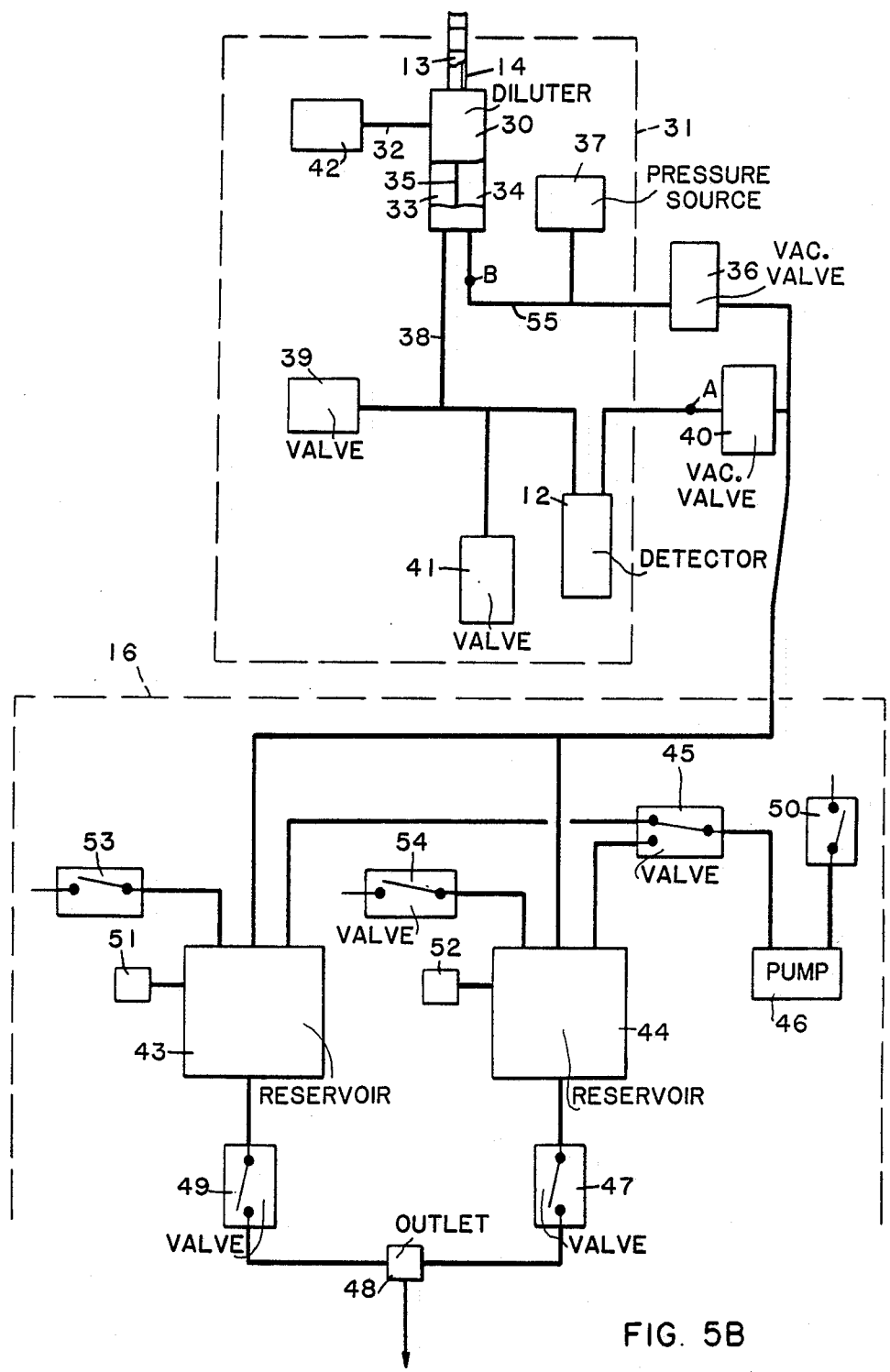

The manifold 29 fashions pulse segments making up the stream 13 in the tubing 14 in pulse segments as shown in the partly broken away section of tubing 14 in FIG. 5B. In the illustrated embodiment the stream 13 is transported to a diluter 30. A diluent is introduced into the diluter 30 through a tube 32 from a suitable source of supply. The sample stream 13 from manifold 29 are the diluent are suitably mixed in the diluter 30 and the product transported to the detector 12 for observation and determination.

The system illustrated in FIGS. 5A and 5B is identified herein as a step pulse fashioning system. The flow of stream 13 is segmented as illustrated in the broken away portion of tube 14.

Force for this segmented flow is provided by the vacuum assembly 16 through vacuum valves 36 and 40. Valves 36 and 40 are vacuum valves which when opened draw the sample or reagent into the system. The volume drawn in is controlled and determined by the period these valves 36 and 40 are open.

In a normal operational sequence of the system of FIGS. 5A and 5B, the vacuum driving it may be in the range of 2 ½ to 15 inches of Hg. The valves are solenoid drive pinch valves. Referring to the operation of the system, reference is made to Table 1 which gives the sequence of operation of the valves and describes the results of each operation. The flow rate is 2 m/1–12 m/1 per minute, preferably 2–4.

The diluter 30 contains two small chambers 33 and 34 separated by a membrane 35. A suitable membrane 35 is a Teflon membrane with a 1.0 micron pore size supported on a non-woven polypropylene sheet.

On the first step of operating Cycle I as charted in Table 1, under the pulling force provided by the vacuum assembly 16 through valve 36 the stream is drawn in the system and the diluter 30 is filled from the manifold 29 by opening a flow through the zero dead volume valves 28a, 28b, and valve 36 with valve 40 closed. The flow of the stream 13 through the diluter 30 is controlled by valves 28a, 28b and 36, which transport at least one pulse segment of the stream to the point A between the diluter 30 and the valved source of air pressure 37 which provides back pressure. In Step 2 the valves 28a, 28b and 36 then close. This positioning of the pulse segments of the integral liquid stream 13 in the sample side of the diluter 30, the tubing 55 provides a reservoir of fashioned segment or segments on the sample side of the membrane in chamber 33 of the diluter 30 to provide a supply of liquid available to be forced through the membrane 35 under the back pressure asserted from the pressure source 37. The pulse segments are fashioned in the operation of the valves 28a and 28b introducing fluid flow into the manifold 29 under the transporting force put in action from the vacuum assembly 16. It will be understood that this fashioning of the pulse segments is directly concerned with the formation of the segmented integral liquid stream described above and illustrated by stream 13 in the embodiment of FIGS. 5A and 5B.

The porous membrane 35 of the diluter 30 is not wetted by either the liquid of the segmented stream 13 or the diluent from tube 32, but is permeable to the liquid of the segmented stream 13 upon the application of back pressure on the reservoir consisting of the segmented stream positioned upstream from point A into the diluter 30.

Next, the Step 3 in the sequence of analysis Cycle I, after providing the reservoir of pulse segments, first valve 40 and valve 42 are opened and then a suitable valve is opened at the source of pressure 37 exerting positive pressure on chamber 34 side of the membrane 35 in the diluter 30. The pulse segment permeates through the membrane 35 and mixing with the diluent in chamber 33 is drawn in a diluted state from the diluter 30 by force exerted from the vacuum assembly 16 by the opening of a main control valve 40 positioned downstream of the detector 12. Varying the amount of back pressure used, alters the amount of the solution transferred to the diluent. The flow of the diluted segmented stream 13 from the diluter 30 in a tubing 38 is controlled by valve 40 and is positioned by transporting the pulse segments to a point A downstream from the detector 12 so as to assure filling the detector 12 with sample or reagent in pulse segments.

The delivery of fashioned pulse segments of sample or reagent to the detector 12 may include suitable valve-controlled apparatus for introducing other substances into the analyzed liquid of the segmented stream. In the embodiment of FIG. 5B valves 39 and 41 illustrate the controls for providing dye through valve 39 and a reagent for forming the appropriate interface through valve 41 from suitable sources.

In one example of an analysis according to this invention in the embodiment of FIGS. 5A and 5B valves 40, and the pressure source 37 are opened to transport diluted pulse segments from the diluter 30 in tubing 38 and form a slug mixture of the pulse segment and the

| Cycle | Stream Structure |
|---|---|
| I | H$_2$O, Acid and Dye |
| II | Sample and Acid |
| III | Sample, Acid and Dye |
| IV | Sample, Standard and Dye |

TABLE 1

| | Valving Sequence | | |
|---|---|---|---|
| Steps | OPEN | CLOSE | Characteristics of Steps |
| | | | CYCLE I |
| 1 | ,28a,28b,36 | | FILL DILUTER AND TUBE TO B |
| 2 | | ,36,28b,28a | FLOW STOPS |
| 3 | ,42,39,40,37 | | FLOW THROUGH CELL TO A SLUG MIXTURE FORMED, WATER, STD, & DYE. |
| 4 | | ,37,40,39,42 | FLOW STOPS |
| 5 | 41,40 | | FORMS INTERFACE, FLOW THROUGH FLOW CELL AND READ A/D, WATER, STD & DYE. |
| 6 | | ,40,41 | FLOW STOPS |
| | | | CYCLE II |
| 7 | ,28b,28c,367 | | FILL DILUTER WITH SAMPLE + ACID. FILL TUBE TO POINT B |
| 8 | | ,36,28c,28b | FLOW STOPS |
| 9 | 42,40,37 | | FLOW BEYOND A SAMPLE IS DILUTED BY ACID AND FORMS SULG |
| 10 | | 37,40,42 | FLOW STOPS |
| 11 | ,41,40 | | FORMS INTERFACE. FLOW THROUGH FLOW CELL AND READ A/D. (sample & acid) |
| 12 | | 40,41 | FLOW STOPS. |
| | | | CYCLE III |
| 13 | ,28b,28c,36 | | FILL DILUTER AND TUBE TO POINT B |
| 14 | | ,36,28c,28b | FLOW STOPS |
| 15 | 42,39,40,37 | | MIXES DYE WITH DILUTED SAMPLE, AND ACID, FLOW THROUGH FLOW CELL TO A |
| 16 | | 40,39,37,42 | FLOW STOPS |
| 17 | 41,40 | | FORMS INTERFACE. FLOW THROUGH FLOW CELL AND READ A/D. (SAMPLE, ACID, & DYE) |
| 18 | | 40,41 | FLOW STOPS |
| | | | CYCLE IV |
| 19 | ,28c,28d,36 | | FILL DILUTER AND TUBE TO B |
| 20 | ——— | 36,28d,28c | FLOW STOPS |
| 21 | 42,39,40,37 | | FLOW THROUGH CELL TO A SLUG MIXTURE FORMED SAMPLE, STD, & DYE. |
| 22 | | 37,40,39,42 | FLOW STOPS |
| 23 | 41,40 | | FORMS INTERFACE. FLOW THROUGH FLOW CELL AND READ A/D (SAMPLE, STD, & DYE) |
| 24 | | 40,41 | FLOW STOPS | valve 40 is closed to position the slug mixture upstream from point A. Then valve 41, valve 42 and valve 40 are opened to introduce through valve 41 a salt to form an interface. The interface flows through the detector 12 and the detector 12 senses and takes measurements. This observed data is transmitted on a line 61 to the analog-to-digital converter 17 in FIG. 1 as described above. With the completion of the readings the control valves 40 and 41 are closed and the sequence of steps of that cycle of analysis has been completed.

The Table 1 charts the sequence of steps in four analysis Cycles I, II, III and IV in a characteristic example of the operation of the apparatus illustrated in the embodiment of FIGS. 5A and 5B. The stream structure for each of these cycles is different thus illustrating the adaptability, versatility and flexibility of the present invention. Each of the Cycles I, II, III, and IV consists of a sequence of six steps with each of the steps related to the states of the valves which fashion the segments and control the transport of the structured stream, and each step characterized by the stream flow.

The stream structures processed in the respective Cycles I, II, III and IV are as follows:

Referring to the operation of the vacuum assembly as embodied in FIG. 5B, two different waste reservoirs 43 and 44 are connected via three-way valve 45 to a vacuum pump 46. With the three-way valve 45 connecting reservoir 43 to the pump 46 and switch 50 in the appropriate position, as illustrated, reservoir 43 is available to be evacuated and simultaneously reservoir 44 is available for exerting the transporting force of the system through valve 40. Thus during an analysis cycle the reservoir, 44 draws the stream 13 in the system of FIGS. 5A and 5B when valve 40 is open. At the close of the cycle, liquid has collected in the reservoir 44 and the observed data has been collected and transmitted from detector 12. At this point in the step sequences after the vacuum valve 40 is closed, a vent valve 54 and a dump valve 47 opens to drain the contents of reservoir 44 through a suitable outlet 48.

The next cycle begins with switch 50 closing to pump down reservoir 43. After the reservoir 43 is pumped down, switch 50 opens, and the valve 45 switches reservoir 44 to vacuum pump 46, while switch 50 is opened. A vacuum is created in reservoir 44 after the vent valve 54 and dump valve 47 are closed. The now evacuated reservoir 43 is available to exert the transporting force in the system. Thus the reservoirs 43 and 44 are alternately evacuated, filled with liquid, dumped and reevaluated. A dump valve 49 drains reservoir 43 through the outlet 48.

The switch 50 is connected to actuate the vacuum pump 46. Switches 51 and 52 are the liquid level detectors for reservoirs 43 and 44, respectively. While valves 53 and 54 provide venting for the respective reservoirs 43 and 44.

Figure 7:
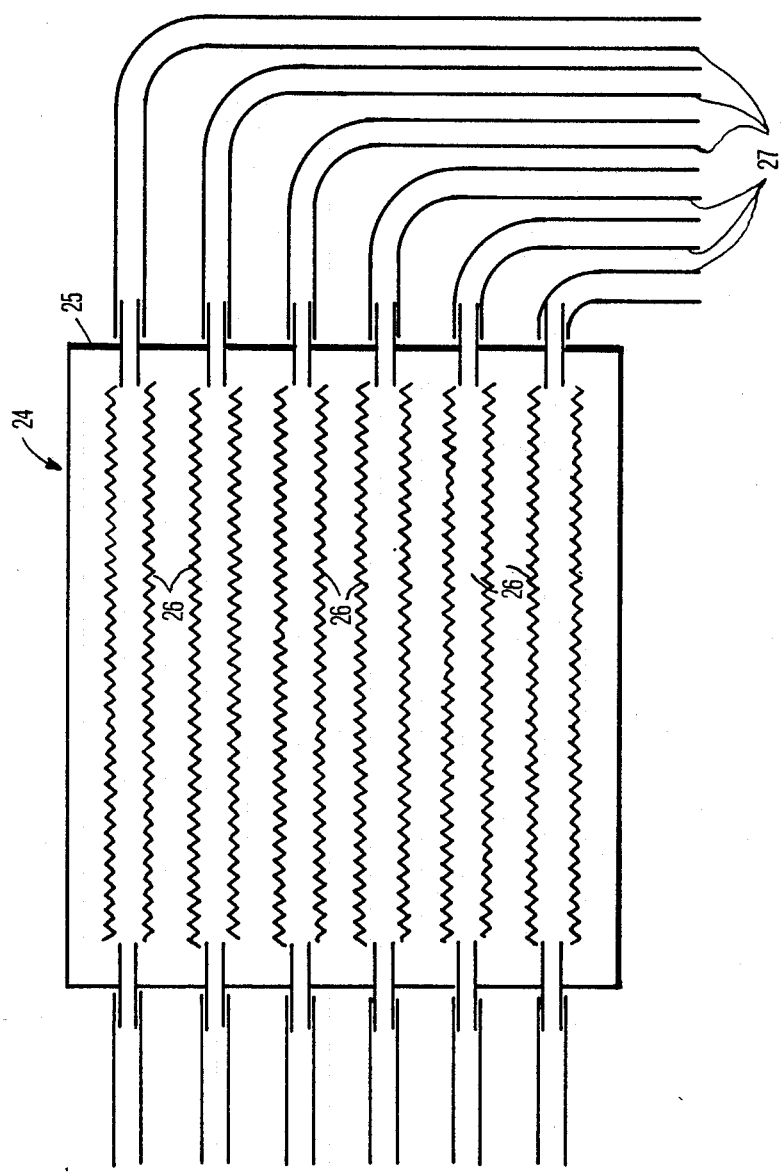
FIG. 7 is a view of a degasser device in the apparatus of this invention.

FIG. 7 is a detailed illustration of the degassing stage of the system embodied in FIGS. 5A and 5B. As noted above, the degasser apparatus 24 has vacuum sealed housing 25 which is suitably evacuated to provide reduced pressures within the housing. The porous tubes 26 conduct the system liquid through the housing 25 while causing gases within the liquid to be removed from the liquid. These tubes 26 may be composed of a number of different materials. The tubes 26 are suitably inert, porous material which is not wetted by the liquid. In one embodiment the tubes 26 are composed of Goretex tubing with 2 micron pores.

FIG. 7 is a detailed illustration of the degassing stage of the system embodied in FIGS. 5A and 5B. As noted above, the degasser apparatus 24 has vacuum sealed housing 25 which is suitably evacuated to provide reduced pressures within the housing. The porous tubes 26 conduct the system liquid through the housing 25 while causing gases within the liquid to be removed from the liquid. These tubes 26 may be composed of a number of different materials. The tubes 26 are suitably inert, porous material which is not wetted by the liquid. In one embodiment the tubes 26 are composed of Goretex tubing with 2 micron pores.

Effective degassing in the degasser 24 is directly related to the difference between the ambient pressure within the housing 25 at which gas passes through the tubing 26 and escapes from the liquid stream and the ambient pressure at which water will seep through tubing 26.

The housing 25 is evacuated to provide a pressure differential of about 10 inches of mercury between the external pressure in the housing 25 and the internal pressure in the tubing 26.

This pressure differential can range from a pressure one-tenth higher in the tubing 26 than the external pressure up to a pressure in the tube which is 12.8 pounds per square inch higher in the tubing.

The length of this tubing 26 is selected or adjusted to allow complete degassing of the liquid within a given time period for the flow rate.

FIG. 8 to 17 show the curve records for the readings obtained from the dispersion data observed from pulse segments fashioned in a system of the nature of the systems illustrated in FIGS. 1, 5A and 5B. The recorded analyzed samples were detected at intervals of 270 $\mu$ sec and the observation recorded. The data was analyzed by a computer using the nonlinear regression algorithm to determine the algebraic model parameters characterizing the methyl or orange dye and alum which was analyzed in the flow system. These parameters were subsequently used with the linear regression algorithm to determine the concentrations of various samples of methyl orange dye and alum.

The plotted curves of these FIGS. 8 to 17 illustrate the indicated values that were detected in the flow cell 12 of the system of this invention by readings taken every 270 $\mu$ sec. and analyzed and processed in the calculations described above. In general these plotted curves show the determination of the composition of the analyzed liquid slugs in the integral but segmented liquid stream at a single interface. The curves are of sigmoidal shape. The curves illustrate the results that were obtained and in analysis by using the liquid integrity of a fashioned stream to provide liquid segments or slugs, for observation, analysis and calculation. These results substantiated achievement of the objects stated above.

Figure 8:
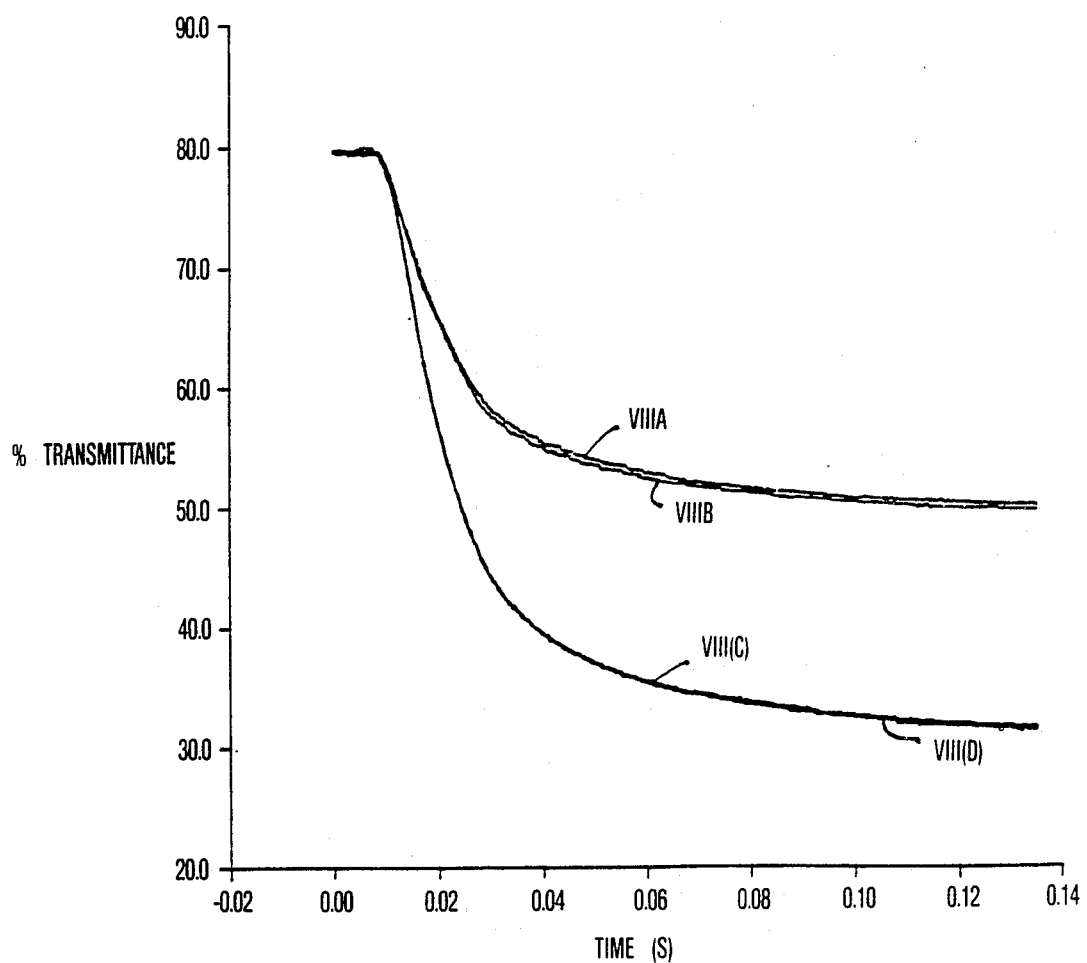
FIGS. 8 to 17 are graphs illustrating the analysis according to the present invention using the step pulse fashioning method.

FIG. 8 is a chart illustrating the application of this invention to the detection and observation of dye concentrations. In graphical form it depicts the curves representing the results of detection of methyl orange dye in step pulse segments of discrete segmented flow conditions. Samples A to B of 2 ppm of methyl orange and samples C and D of 4 ppm of methyl orange were passed in segments through the flow cell 12 and transmittance values against time were detected as illustrated in the plotted curves A, B, C and D of FIG. 8.

Figure 9:
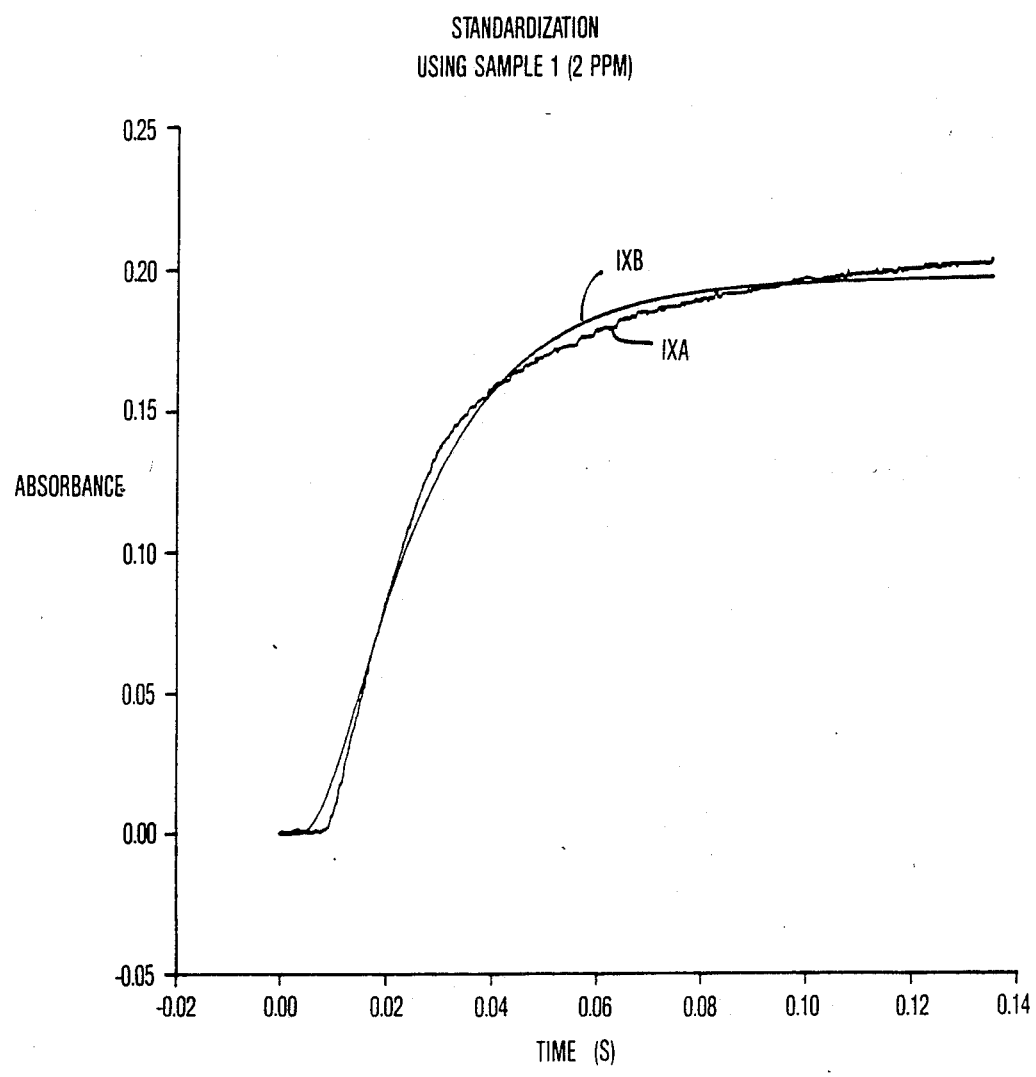

FIG. 9 shows the results of standardization of the apparatus of the nature of FIGS. 1, 5A and 5B for detecting concentrations of methyl orange dye using Sample 1 having a concentration of 2 parts per million of methyl orange introduces into the system.

FIG. 9 illustrates the results from a determination from a sample 1 of 2 ppm drawn through the system. This determination is a standardization procedure in accordance with the descriptions for providing a model prediction curve related to methyl orange specimens. The recorded data was processed in a computer by non-linear regression to determine model parameters $P_1$, $P_2$, $P_3$ and the determination of the methyl orange concentration. This is non-linear regression of the sample over absorbance-time data detected in the cell 12 according to the calculations set forth above. The curves which represent a large number of readings, represent the plot of the concentration of methyl orange dye detected in the sample 1 by detection and observation at the interface between the sample segment and the reagent in the manner described above.

Curve IX$a$ illustrates the observed and detected data and IX$b$ represents the model prediction curve.

In the non-linear regression of the standardization procedure illustrated by FIG. 9 by the equation (2) above the observed, analyzed and calculated results provide the following Parameter P1 - 0.6856 ps Parameter P2 - 0.0231 sec. ps Parameter P3 - 0.0984 units of reciprocal ppm ps which were parameters for calibration and the results of the standardization procedure. In this non-linear regression the $c$Std of equation (2) is 2 ppm.

FIGS. 10–13 illustrate the analysis of an unknown sample of methyl orange using the linear regression of equation (3) to (4). Curve X$a$ depicts the observations converted to absorbance obtained by the analysis of Sample 1. Curve X$b$ is the model prediction curve for that sample and indicates that concentration is 2.0 ppm because of the linear regression described in equations (3) and (4).

FIGS. 14 thru 17 illustrate the example of applying the technique to the chemical analysis of standard addition and corresponds to the instrument described in FIGS. 1, 5A and 5B and the chart of Table 1.

Figure 14:
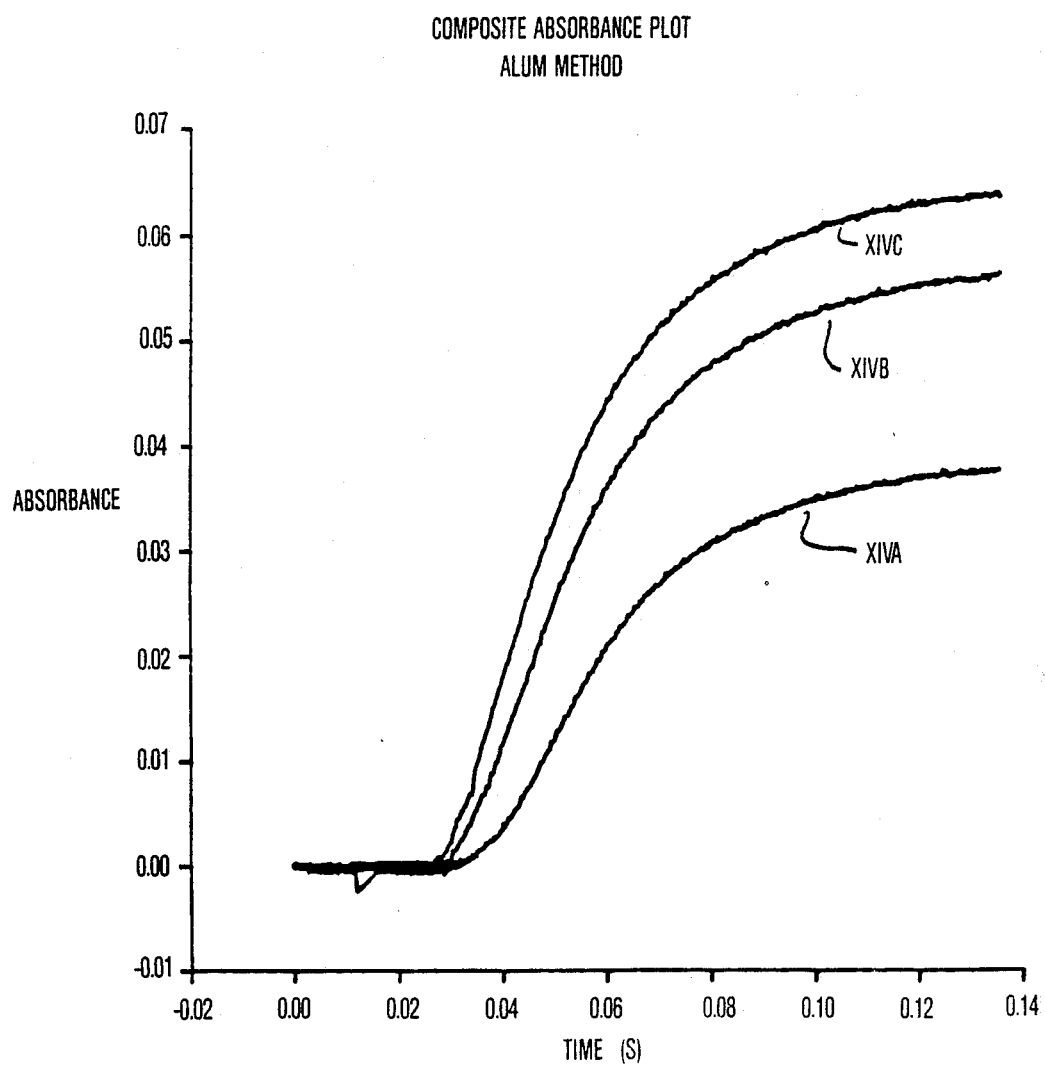
Figure 15:
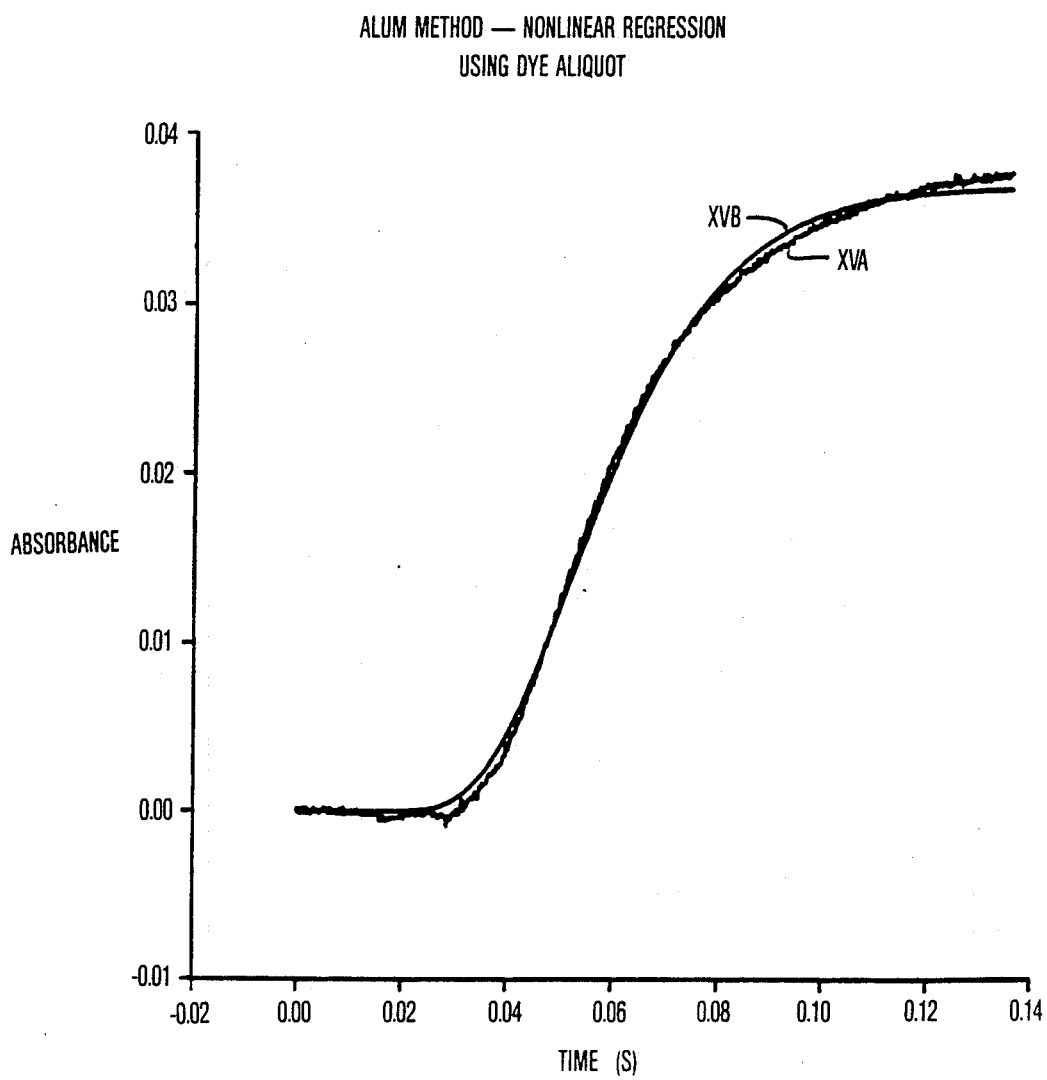
Figure 16:
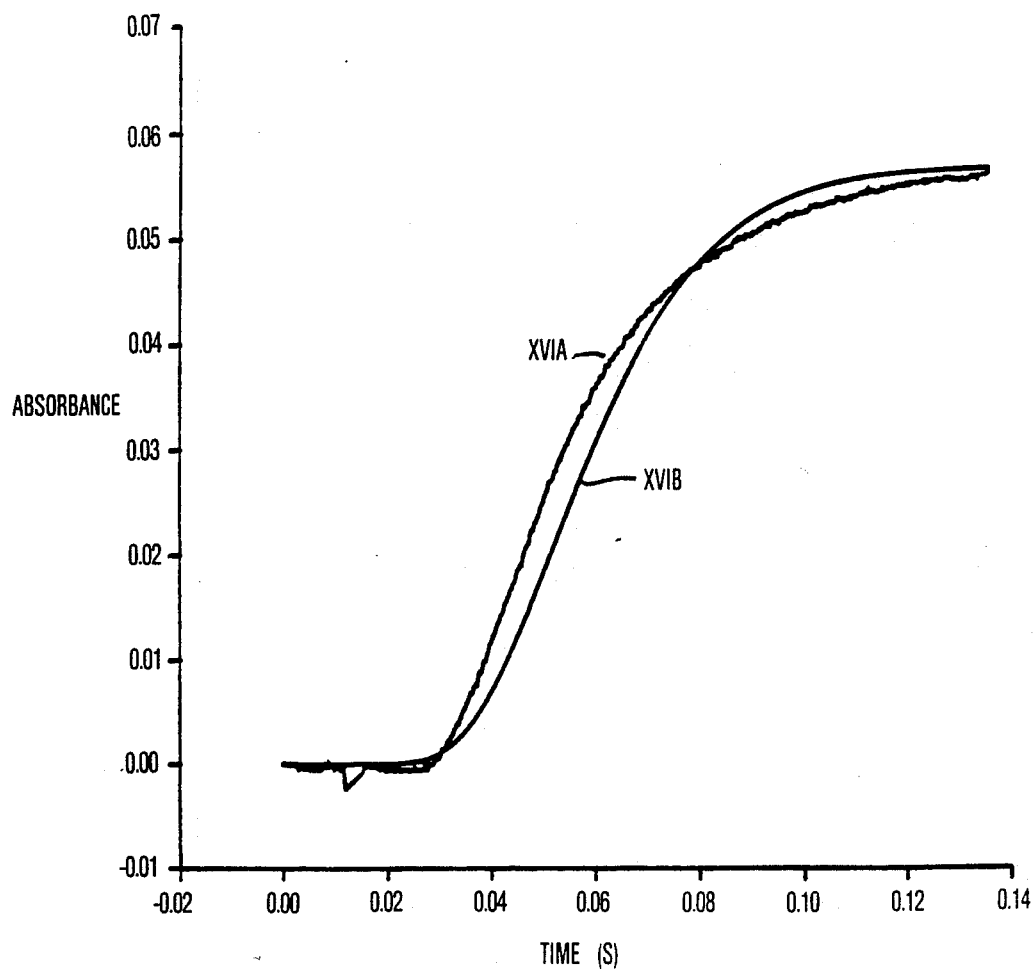

In FIG. 14 curve XIV$a$ is the calibration curve to obtain the flow parameters, curve XIV$b$ is the curve of the analysis of the sample and curve XIV$c$ pertains to the analysis of the sample which contains in addition an added standard FIG. 15 shows the standardization of the instrument using the dye aliquot using equation (2). The parameters determined were $P_1 = 4.5058$ ps $P_2 = 0.0579$ sec. ps $P_{3C} = 0.0369$ ps FIG. 16 represents linear regression analysis done on the sample segment as represented by curve XIV$b$ of FIG. 14. The $P_3C$ is 0.05694.

Figure 17:
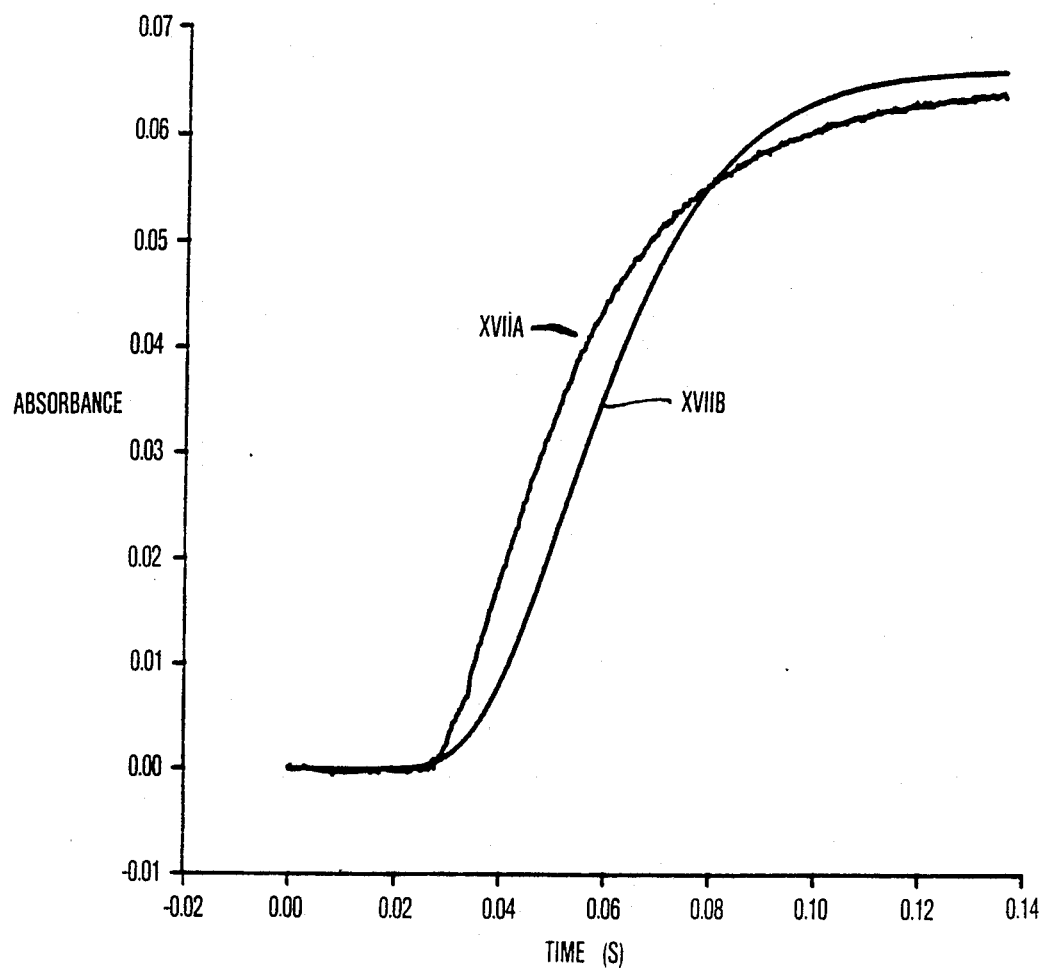

FIG. 17 represents linear regression analysis done on the sample plus added standard segment represented by curve XIV c.

The $P_3C$ value was 0.6609.

The result of the three analyses are combined using the following equation to determine the sample concentration of alum $$C_{samp} = \frac{(P_3C)_{SD} - (P_3C)_D}{(P_3C)_{SSD} - (P_3C)_{SD}} C_{std}$$

The result was 421 ppm as related to the known concentration of 400ppm.

FIGS. 18 to 23 show curve records for readings obtained from dispersion data observed from the use of conventional flow injection instrument to analyze in accordance with this invention. In this embodiment analysis is carried out according to this invention by using conventional flow injection apparatus to prepare a mode prediction curve for the determination of the characteristics of a component in the flow injection analyzer apparatus.

Figure 18:
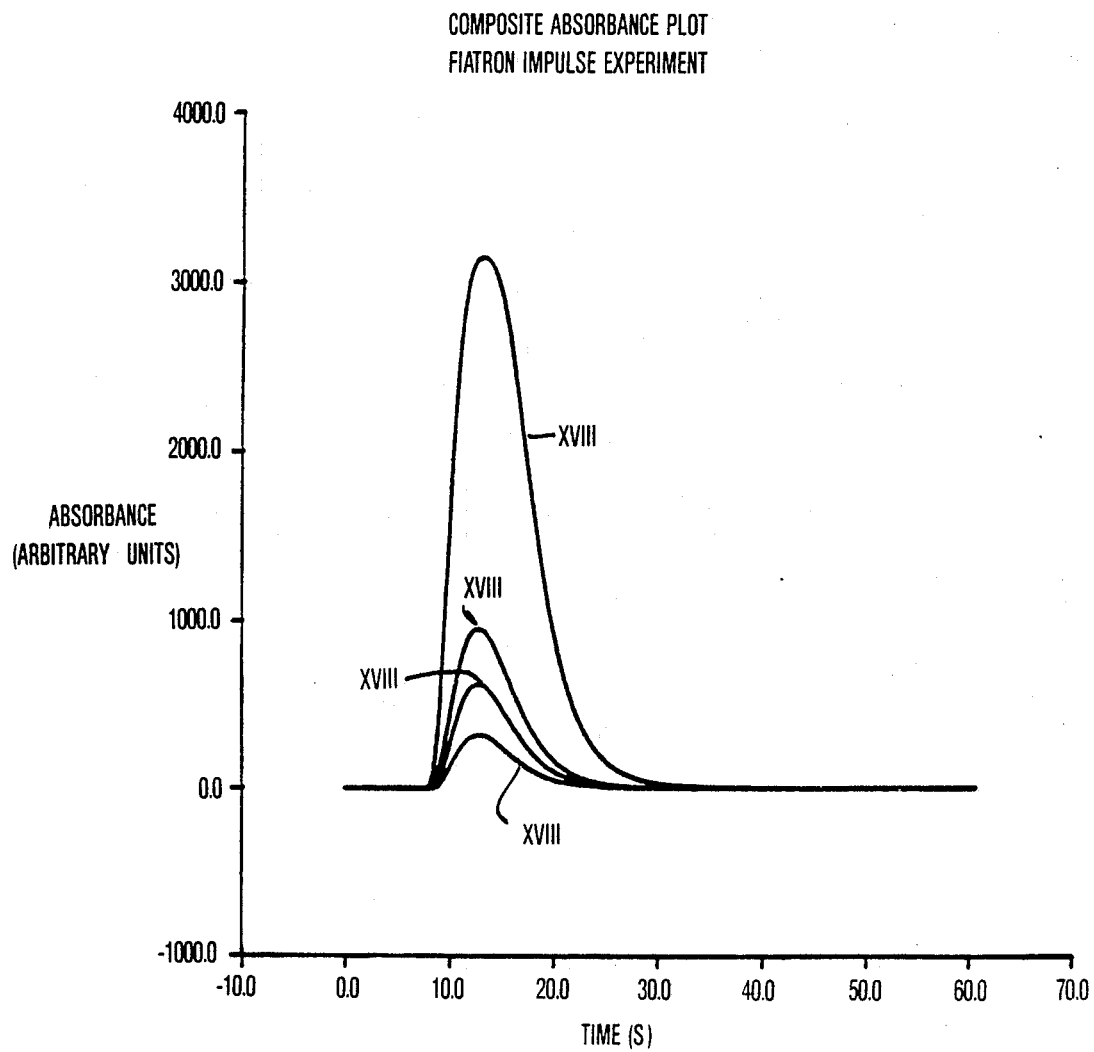
FIGS. 18 to 23 are graphs illustrating another embodiment of this invention in which impulse injection is used in a conventional flow injection instrument using peristaltic pumping.
Figure 19:
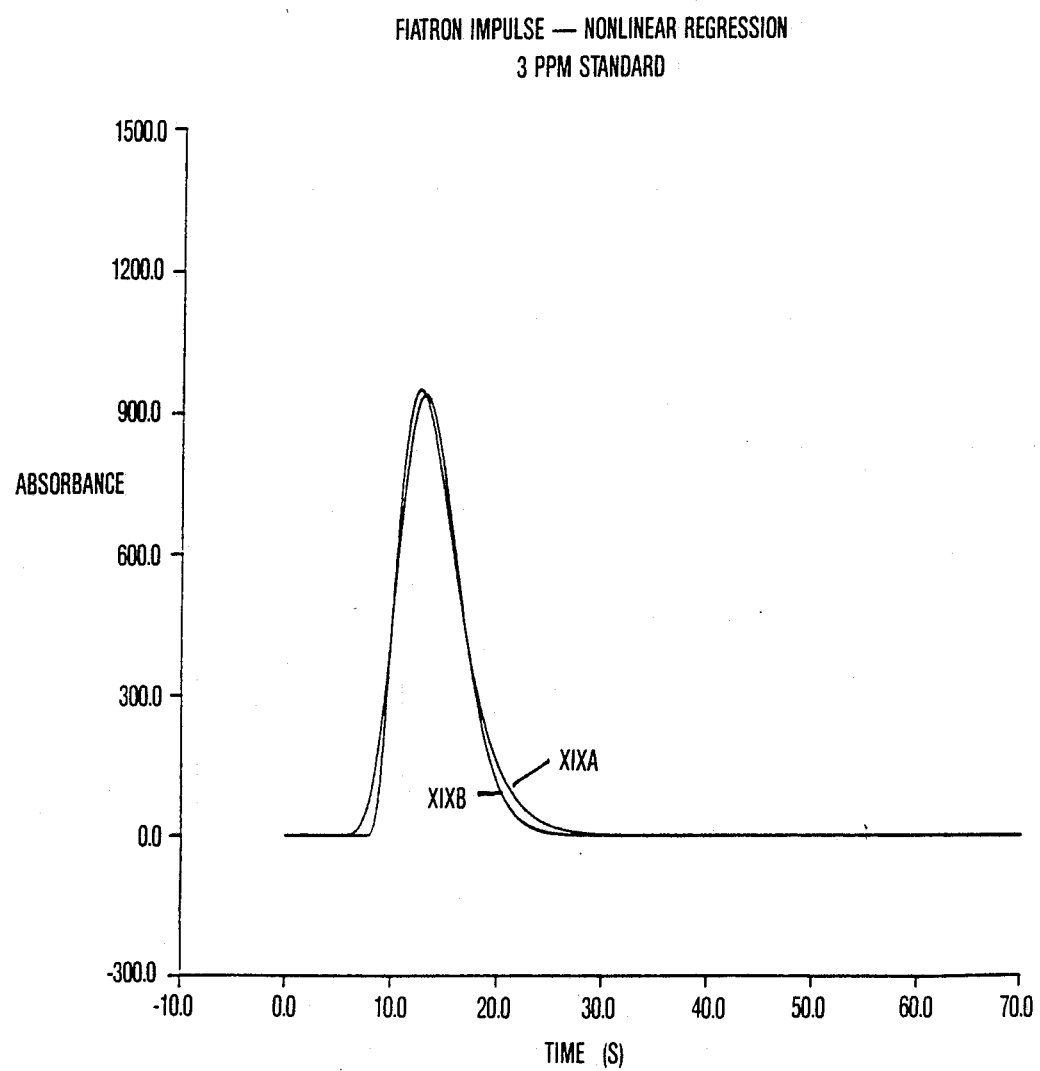
Figure 20:
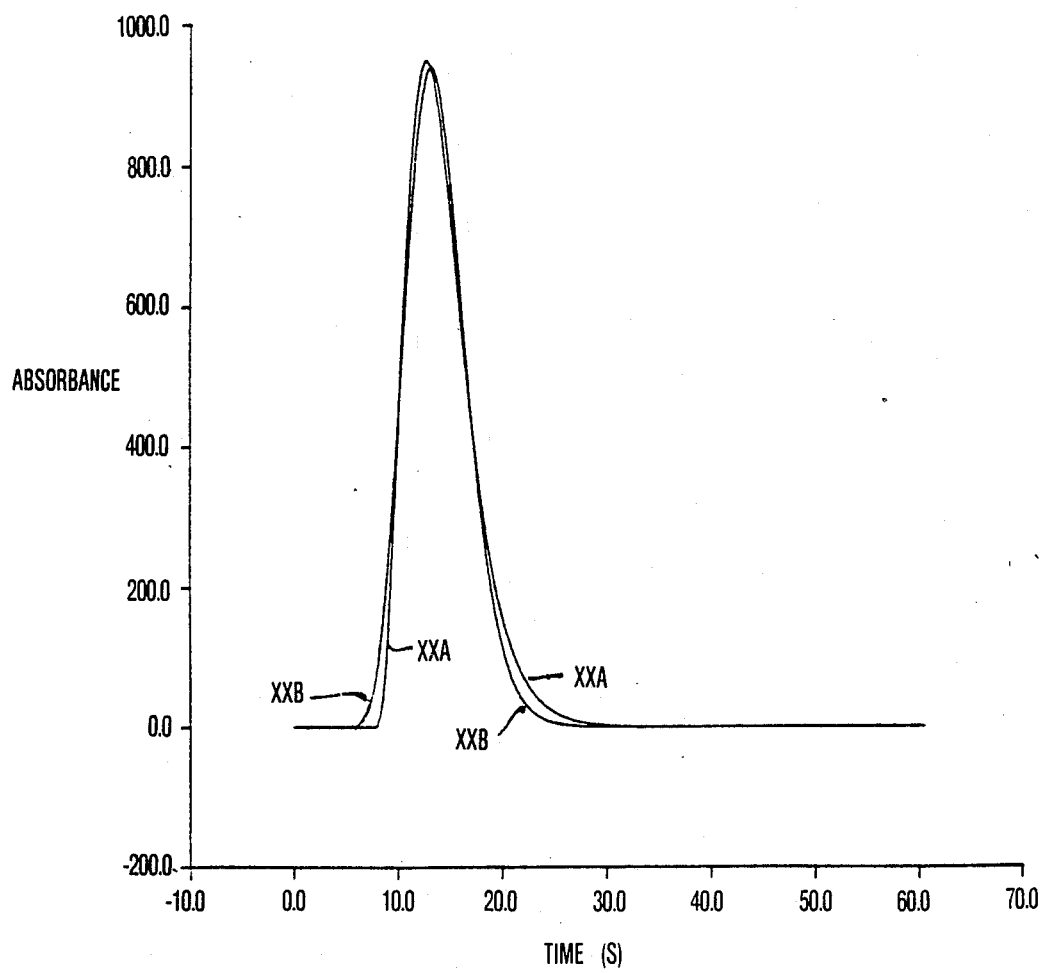

FIG. 18 illustrates curves depicting the experimental observations of absorbance for methyl orange dye in four concentrations, 1, 2, 3 and 10 ppm, curves XVIII($a$), XVIII($b$), XVIII($c$), and XVIII($d$) respectively. FIG. 19 depicts the observed data curve XIX$a$ for the 3 ppm methyl orange injection which was used as the standard. This curve XIX$a$ represents the observation of the absorbance as a function of time observed by the photodetector. Curve XIX($b$) represents the model prediction curve resulting from non-linear regression of the curve XIX$a$ data using the equation(5). The close coincidence of curves XIX$a$ and XIX$b$ is noted. The parameter values obtained were $P_1 = 12.74$ ps $P_2 = 13.29$ sec ps $P_3 = 1682$ ps FIG. 20 depicts the analysis of a sample using the model parameters obtained in the standardization step described above. Curve XX$b$ is the same as curve XIX$b$ for the 3 ppm generated by different means, namely linear regression. Curve XX$a$ is the result of the observation of the 3 ppm sample of FIG. 20.

Figure 10:
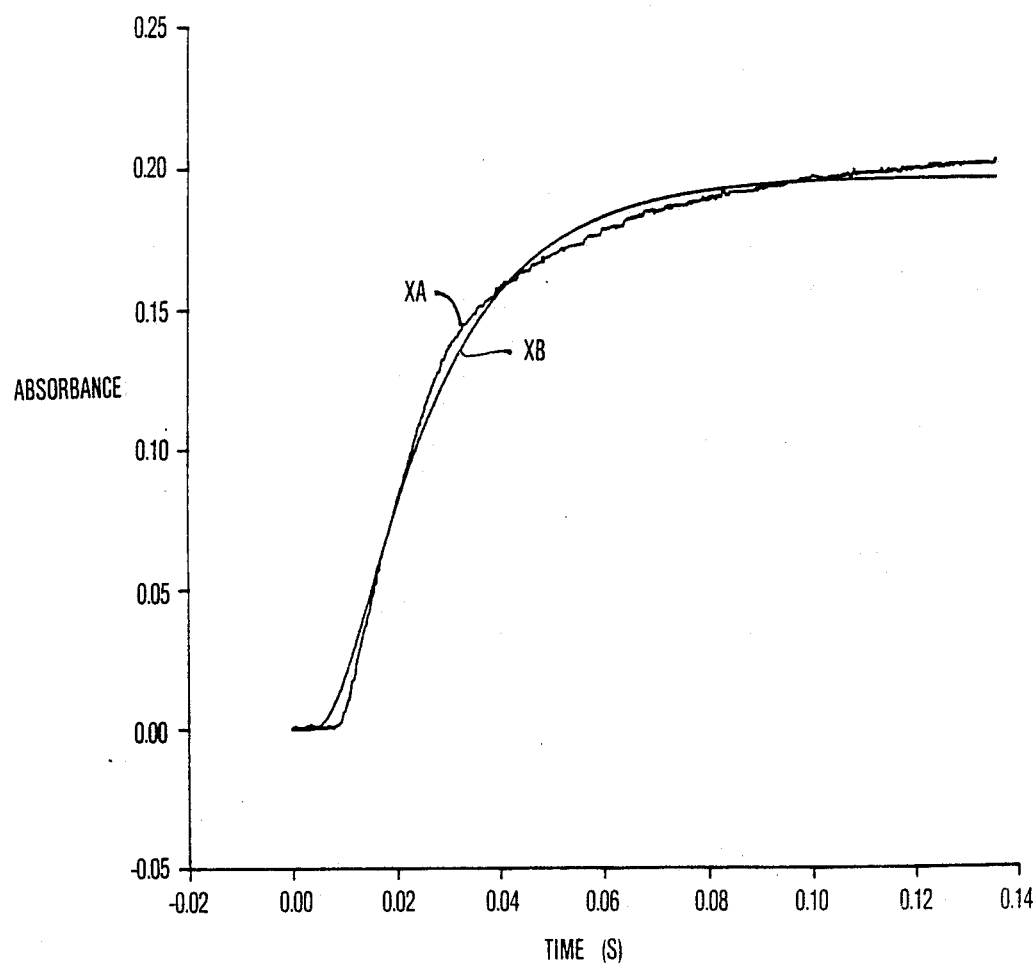
Figure 11:
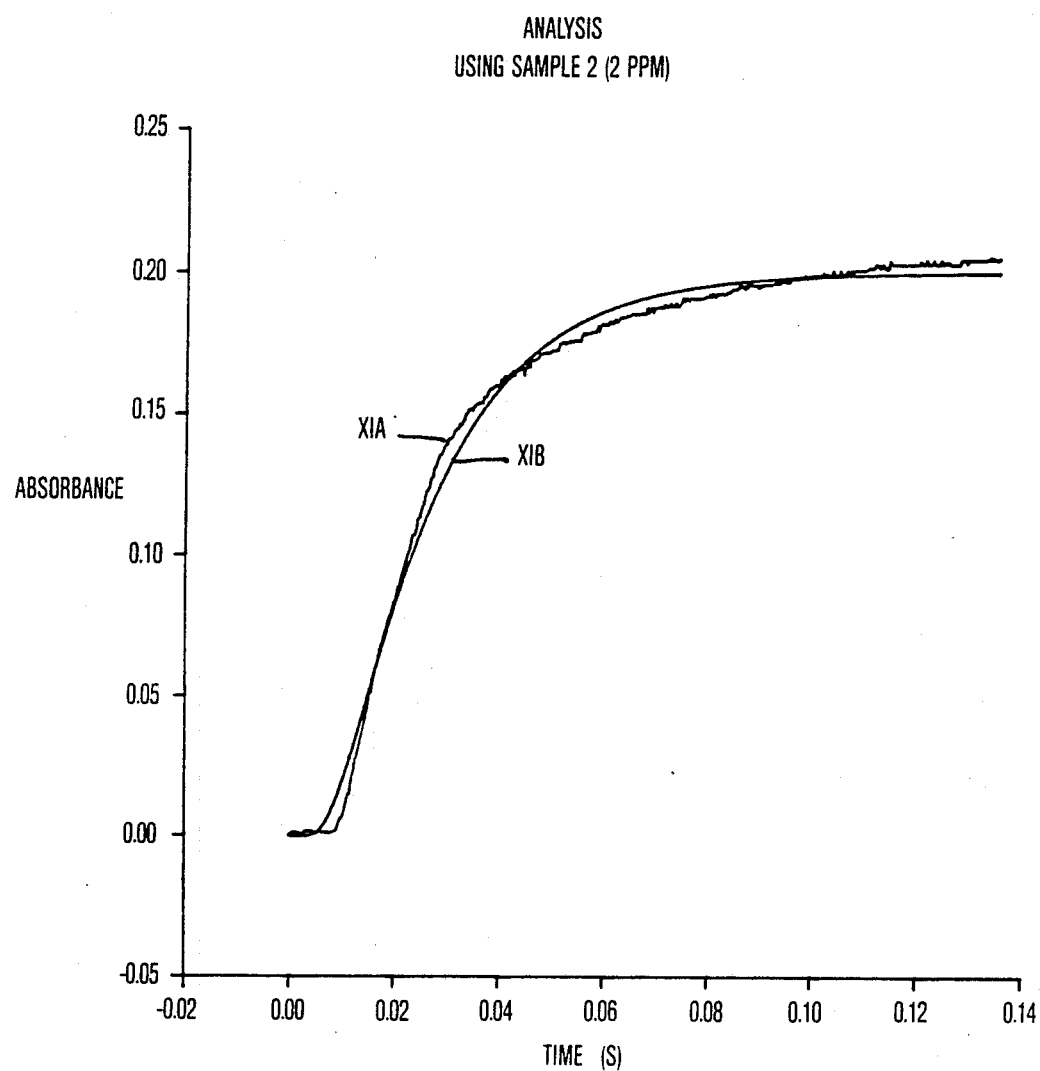
Figure 12:
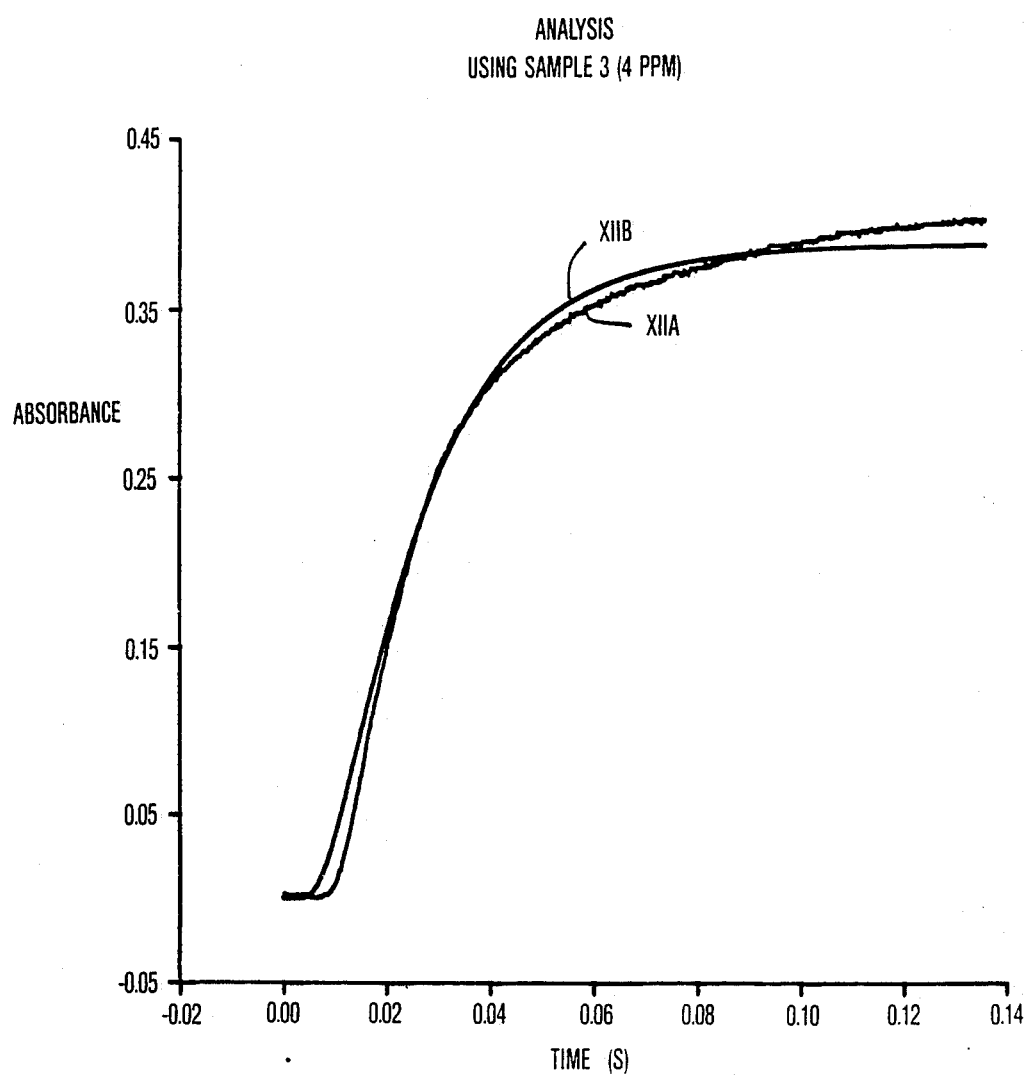
Figure 13:
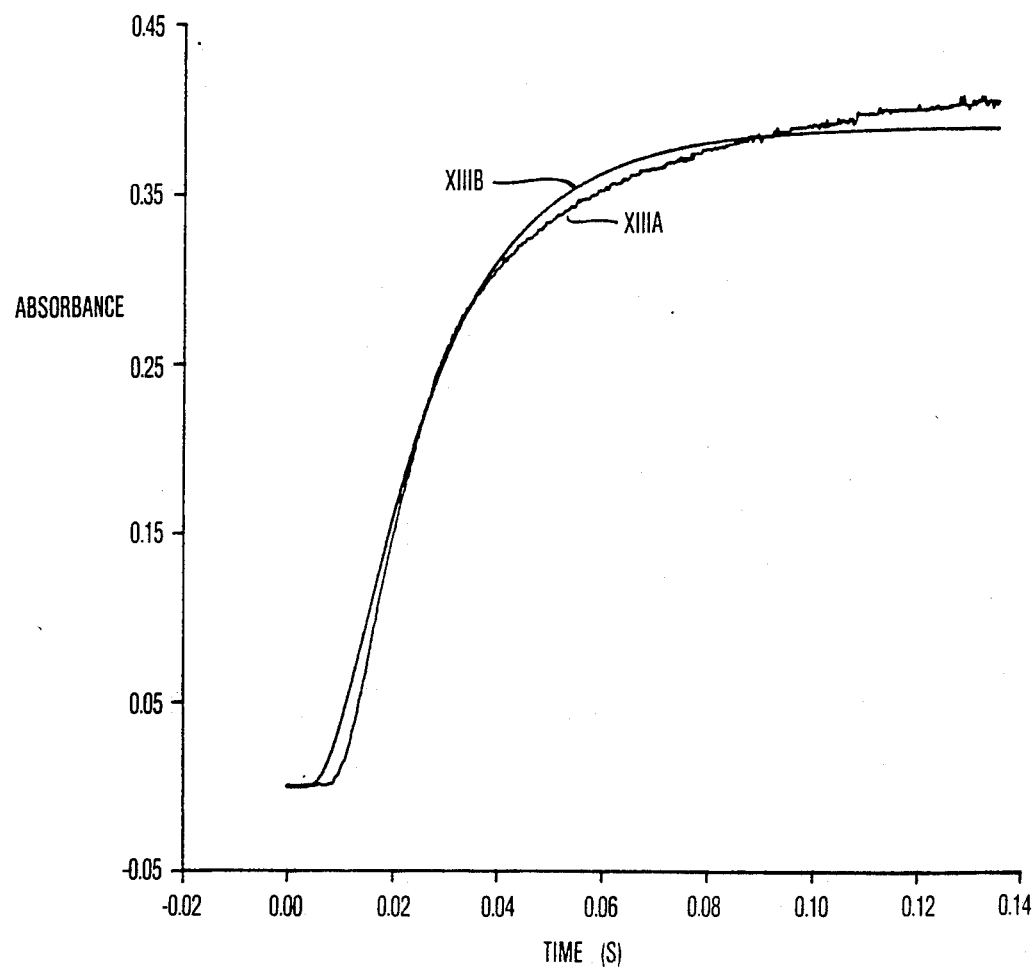
Figure 21:
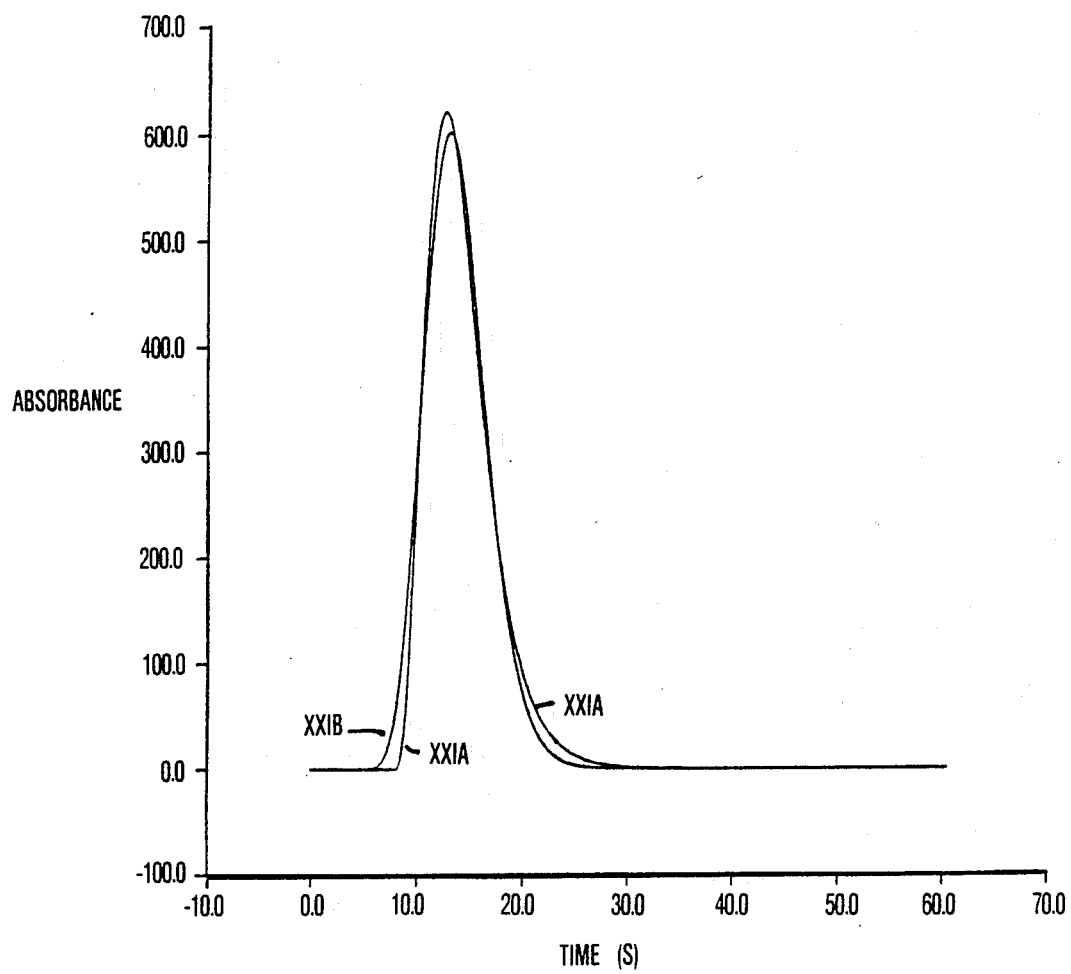
Figure 22:
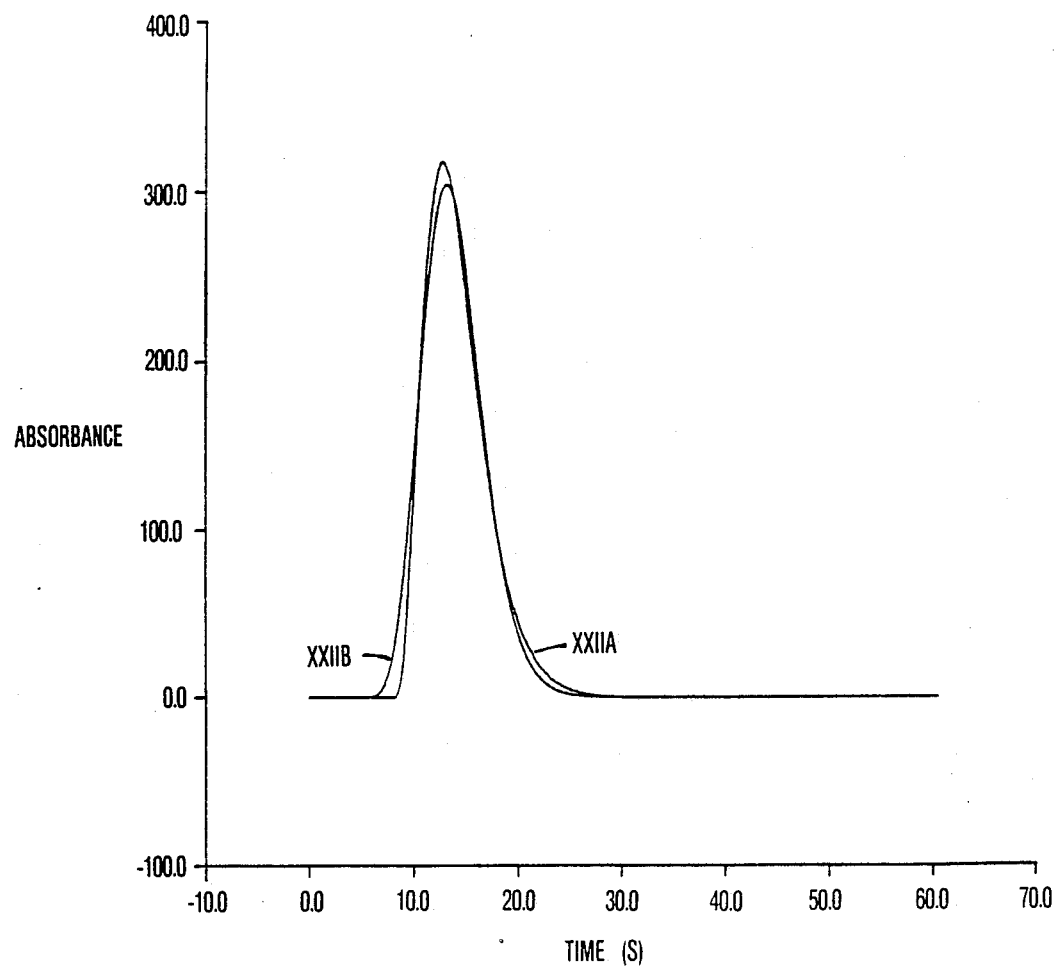
Figure 23:
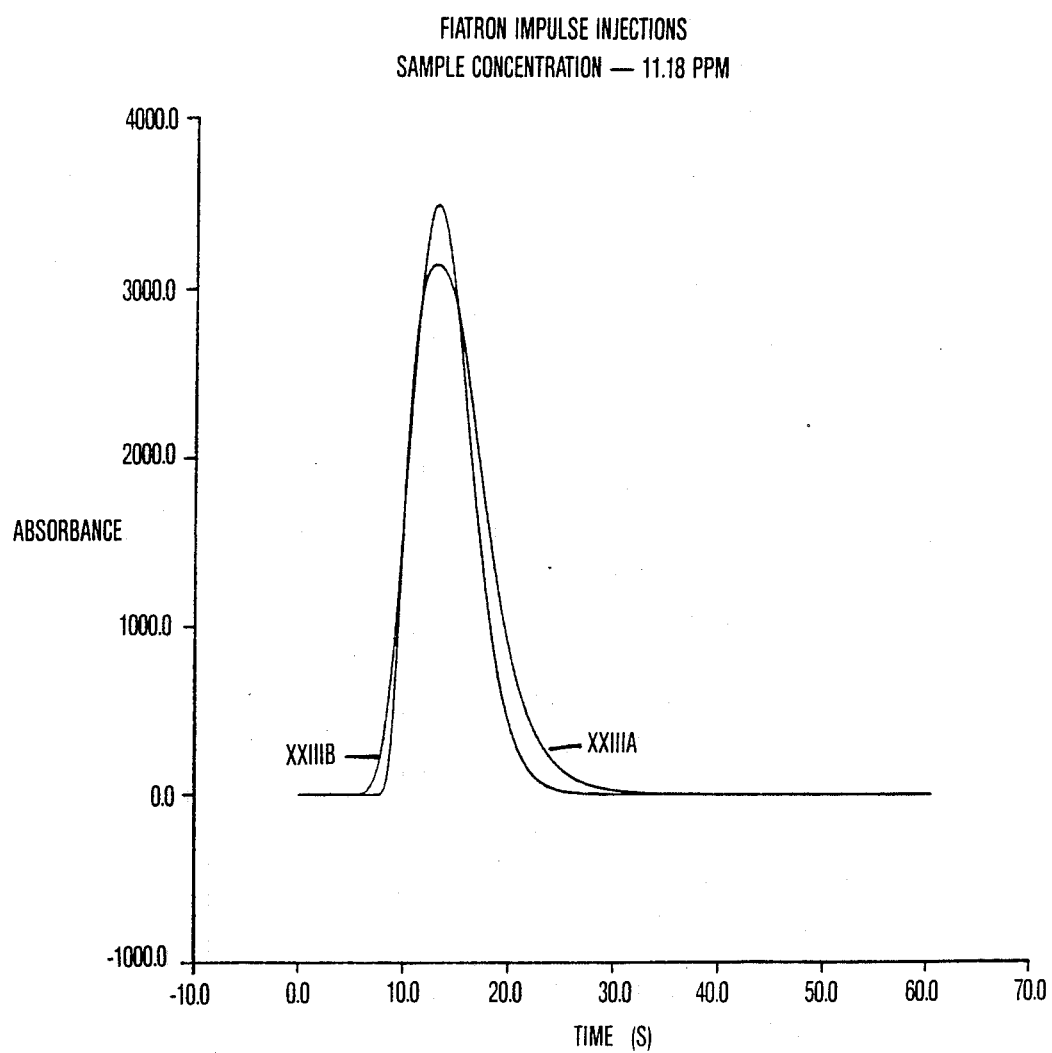

FIGS. 21, 22 and 23 illustrate examples of carrying out the analysis similar to that of FIG. 20 with samples of the concentration of 2 ppm for FIG. 21, 1 ppm for FIG. 22, and 10 ppm for FIG. 23. The results are listed in the legends in the respective figures.

Among other advantages of the present invention it is to be noted that in the analysis it is not necessary to analyze the entire curve to do the analysis. All that is needed is any portion of the curve that is illustrated in the figures, providing that the model is sensitive to that section.

Further, when the measured quantity is not a linear function of concentration it is still possible to do the analysis with only one additional calibration point.

What is claimed is:

1. An analyzing apparatus for detecting the properties and composition of injected liquid sample in a non-air segmented liquid stream, comprising in combination in a flow system:

a supply means for providing liquid samples, reactants and reagents to said system;

conduit means for receiving liquid samples, reactants and reagents from said supply means;

vacuum means connected to and for creating a force for driving said liquid samples, reactants and reagents from said supply means through said conduits and through a detector with a combination of valves controlling the vacuum force on said liquid samples, reactants and reagents to form a non-air segmented, integral liquid stream of non-continuous flow;

said liquid stream consisting essentially of samples, reactants or reagents in the absence of air segments in the stream whereby liquid integral segments interface with each other, said apparatus including:

means for injecting into said stream a sample so as to provide an interfacial zone of a step pulse fashioned of said liquid in the non-air segmented, integral stream of non-continuous flow;

means for observing properties of at least one concentration of a dispersed liquid at an interfacial zone of a step pulse and providing data in digital signals correlated to said observed properties;

means for the observation of known property values of an injected standard being drawn through a detector which means generates signals representing parameter values characteristic of the flow system, summarized in digital form and processing said generated signals to evaluate properties of the dispersed liquid at the interfacial zone of samples so fashioned and drawn through said detector;

means for performing in a computer calculation from the data obtained from the known specimen by mathematical evaluation to determine algebraic model parameters which characterize the flow system;

storage means for storing digital signals and said model parameter values characteristic of the flow system in digital form;

means for repetitively performing calculations in the computer on said data obtained from the interfacial zones of injected liquid samples to obtain values of a property of each sample; and means responsive to said characteristic values of the model parameters for rapidly recording property values of the samples.

2. Apparatus as claimed in claim 1 wherein all the detected data is recorded and processed.

3. An analyzing apparatus as claimed in claim 1 wherein said means for performing in a computer calculations on the data to include non-linear regression calculations to determine said algebraic model parameters.

4. Apparatus as claimed in claim 3 having model parameters obtained and stored in said storage means, wherein
said apparatus has means for comparing therewith detected data after non-linear regression of an interfacial zone of a step pulse injection.

5. A method for analyzing liquid samples in a detector for the contents of liquid compositions, comprising the sequential steps of:
supplying liquid samples, and reactants or reagents;
creating a vacuum force for driving said liquid samples, and reactants or reagents through a detector with a combination of valves controlling the vacuum force on said liquid stream and forming a non-air segmented, integral liquid stream of non-continuous flow consisting essentially of samples, and reactants or reagents in the absence of air segments in the stream;
injecting a sample of known properties into said non-air segmented integral liquid stream and forming an interfacial zone of a step pulse comprised of said liquid sample in a non-air segmented, integral stream;
observing properties of the concentration of the dispersed liquid of the known sample at the interfacial zone in a series of observations and providing data in digital signals correlated to said observed properties;
performing in a computer calculations on the data obtained from the known samples, obtaining from a mathematical evaluation algebraic model parameters which characterize the flow system;
storing digital signals and said model parameter values characteristic of the flow system in digital form;
obtaining repetitively data from interfacial zones of step pulses of liquid samples repetitively injected in the non-air segmented, integral stream of non-continuous flow; and
repetitively performing in said computer calculations, from the obtained data, to obtain values of a property of each sample.

6. The method for analyzing liquid samples as claimed in claim 5
including the step of performing in a computer calculations on the data obtained from the known samples a non-linear regression to obtain said algebraic model parameters.

7. A method for analyzing liquid samples in a detector for the contents of liquid compositions with a computer, comprising the sequential steps of:
providing a supply of liquid samples and reactants or reagents;
creating a force for driving said liquid samples, and reactants or reagents through a detector in a liquid stream;
controlling the force on said liquid stream and forming a non-air segmented, integral liquid stream of continuous flow consisting essentially of samples, reactants or reagents in the absence of air segments in the stream;
injecting a sample of known properties into said non-air segmented, integral liquid stream and forming an interfacial zone of a step pulse comprised of said liquid sample in the non-air segmented, integral stream;
observing properties of the concentration of the liquid dispersion of the known sample at the interfacial zone in a series of observations and providing data in digital signals correlated to a series of observed properties to said computer;
performing in the computer non-linear regression calculations to determine algebraic model parameters which characterize the flow system and the detector, which equation is $$y(t) = \tfrac{1}{2} P_3 C_o \left[ 1 - erf\left( \frac{1 - t/P_2}{2\sqrt{P_1 t/P_2}} \right) \right]$$

$P_1$, $P_2$ and $P_3$ being three parameters, $C_o$ characteristic of the specimen sample and $Y_t$ the detected property;
storing said digital signals and said model parameter values characteristic of the flow system and the detector in digital form;
obtaining repetitively data from interfacial zones of step pulses of liquid samples repetitively injected in the non-air segmented, integral stream of non-continuous flow; and
repetitively performing the calculations in the computer on the obtained data to obtain values of a property of each sample.

8. An analyzing apparatus for detecting the properties and composition of injected liquid samples in a non-air segmented liquid stream; comprising in combination in a flow system:
a supply means for providing liquid samples and reactants or reagents,
conduit means for receiving liquid samples from said supply means,
means connected to, and for creating a force for driving, said liquid samples and reactants or reagents from said supply means through said conduits and through a detector with a combination of valves controlling the force on said liquid samples to form a non-air segmented, integral liquid stream of non-continuous flow:
said liquid stream consisting essentially of samples, reactants or reagents in the absence of air segments in the stream whereby liquid integral segments interface with each other, said apparatus including:
means for injecting a sample so as to provide an interfacial zone of a step pulse fashioned of said liquid in the non-air segmented, integral stream of non-continuous;
means for observing properties of at least one concentration of a liquid dispersion at an interfacial zone of a step pulse and providing data in digital signals correlated to said observed properties;
means responsive to the observation of known property values of an injected standard being drawn through the detector which means generates signals representing parameter values, summarized in digital form;
means for processing said generated signals to evaluate properties of the liquid dispersion of the interfacial zone of samples so fashioned and drawn through the detector;
means for performing in a computer calculations on the data obtained from the known specimen said calculations including non-linear regression for determining the parameters $$y(t) = \tfrac{1}{2} P_3 C_o \left[ 1 - erf\left( \frac{1 - t/P_2}{2\sqrt{P_1 t/P_2}} \right) \right]$$

$P_1$, $P_2$ and $P_3$ being three parameters, $C_o$ characteristic of the specimen sample and $Y_t$ the detected property;

storage means for storing digital signals, said digital signals summarizing in digital form model parameter values characteristic of the flow system and detector;

means for repetitively performing in the computer calculations from data obtained from the interfacial zones at injected liquid samples to obtaining values of a property of each sample,
which is $$C_s = \frac{\sum\limits_{i=1}^{n} y_i x_i}{\sum\limits_{i=1}^{n} X_i^2}$$

$$X_i = \tfrac{1}{2} P_3 \left\{ 1 - erf\left[ \frac{1 - t_i/P_2}{2\sqrt{P_1 t_i/P_2}} \right] \right\}$$

and said system comprising means responsive to said obtained values for rapidly obtaining data and recording property values of the samples.

* * * * *